United States Patent [19]

Iguchi et al.

[11] Patent Number: 5,043,006
[45] Date of Patent: Aug. 27, 1991

[54] BENZAMIDE DERIVATIVES AND PLANT GROWTH REGULANTS CONTAINING THEM

[75] Inventors: Hiroyuki Iguchi; Kaoru Kasahara; Shinichi Matsuno; Norimasa Yokoyama; Takeo Motegi, all of Tokyo, Japan

[73] Assignee: Hodogaya Chemical Co., Ltd., Tokyo, Japan

[21] Appl. No.: 450,440

[22] Filed: Dec. 14, 1989

[30] Foreign Application Priority Data

Dec. 23, 1988 [JP] Japan ................. 63-323568

[51] Int. Cl.$^5$ ............................. A01N 37/44
[52] U.S. Cl. ........................... 71/76; 71/111; 71/115; 71/118; 560/47; 562/456; 564/156
[58] Field of Search .......... 560/47; 562/456; 564/156; 71/111, 115, 118, 76

[56] References Cited

U.S. PATENT DOCUMENTS 3,340,042  9/1967  Schwartz et al. .
4,284,813  8/1981  Takematsu et al. .
4,878,942  11/1989  Motegi et al. .................. 71/109

FOREIGN PATENT DOCUMENTS 0281120  9/1988  European Pat. Off. .

*Primary Examiner*—Bruce Gray
*Attorney, Agent, or Firm*—Oblon, Spivak, McClelland, Maier & Neustadt

[57] ABSTRACT

A benzamide derivative of the formula:

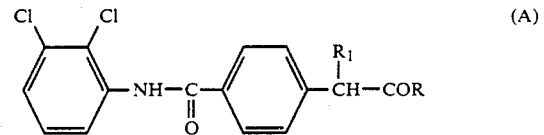

wherein $R_1$ is hydrogen or methyl, and R is hydroxyl, $C_1$-$C_6$ alkoxy, alkenylalkoxy, alkoxyalkoxy, amino, $C_1$-$C_4$ monoalkylamino, monoalkenylamino, dialkylamino or O-cat wherein cat is a metal, ammonium or an organic cation.

3 Claims, No Drawings

BENZAMIDE DERIVATIVES AND PLANT GROWTH REGULANTS CONTAINING THEM

The present invention relates to certain specific benzamide derivatives and plant growth regulants containing such benzamide derivatives.

As plant growth regulants, it has been known to utilize plant hormones or compounds having similar activities, or to utilize compounds which exhibit antagonistic activities against gibberellin or auxin or which inhibit biosynthesis by plant hormones in the plant bodies. The latter agents may be divided into folier treatment agents and soil treatment agents.

The folier treatment agents have a long history and include maleic acid hydrazide (MH), 2-chloroethyl trimethylammonium chloride (CCC) and (N-dimethylamino)succinamide acid (SADH), as typical examples. MH is useful to control axillary buds of tabacco or to improve storage stability of onion. CCC is used to reduce lodging of wheat or as a dwarfing agent useful in the field of horticulture. SADH is used in the fields of dwarfing, growth suppressing or induction of flower buds for fruit trees or green trees.

The soil treating agents include many agents which have been developed in relatively recent years. Many of them, such as triazole type agents, have very strong activities, which last for a long period of time. As a typical example, (2RS,3RS)-1-(4-chlorophenyl)4,4-dimethyl-2-(1H-1,2,4-triazol-l-yl)pentan-3-ol (paclobutrazol) is used for reducing lodging of rice, for growth control of lawn, or for dwarfing or inducing flower buds in the field of horticulture.

In general, the effects of such plant growth regulants are very much influenced by the species and growing stage of the plant, or by the weather or soil conditions. Therefore, various agents are selectively used in various fields. The compounds of the present invention have activities antagonistic to plant hormones and belong to folier treatment agents exhibiting such activities.

Conventional folier treatment agents are usually poor in their activities and require a large dose. Further, depending upon the plants, the sensitive period is limited, and the optimum period of treating time is narrow. If they are used at a high concentration to increase their activities, phytotoxicity such as withering due to the high concentration is likely to be brought about, and the applicable range of plant species due to variation in the sensitivity tends to be narrow. For example, MH has strong side effects and is likely to bring about phytotoxicities such as whitening or withering. CCC is useful as a lodging reducing agent, but the optimum period for treatment is narrow for wheat, and the activities are poor for rice or barley.

In the case of the horticultural plants cultivated in pots, weak activities of an agent such as SADH, may be supplemented since the agent can be used as a folier and soil treatment agent. However, in the case of green trees cultivated on earth, the weakness of the activities can hardly be supplemented.

On the other hand, soil treatment agents are susceptible to the influence of the nature of soil or the amount of rain. If they are ineffective or applied excessively, they remain in soil and tend to adversely affect the subsequent crops or the cultivation of subsequent years, or in the case of parmanent crop plants, they are likely to terminate the growth of the crop plants for several years.

These drawbacks have been solved to a large extent by the activities of phenoxy acetic acid (propionic acid) benzamide derivatives (Japanese Unexamined Patent Publications No. 216803/1988 and No. 29348/1989). However, these agents are still inadequate, when handling efficiency and a high level of activities are required. For example, when they are used as lodging reducing agents for rice, the application tends to be non-uniform since the difference in the activities due to the variation of dose is large. From the viewpoint of the sensitivity, wheat and barley have poor sensitivity as compared with rice, and the same applies to lawn grass of cold area type. The sensitivity of egg plants is also poor. Their effects for controlling axillary buds of tabacco are poor. Also in the horticultural field, they have had a problem that it is difficult to control the dwarfing effects and the influence to the flowers.

The present inventors have conducted extensive researches on the plant activities of novel benzamide derivatives and have found that certain specific benzamide derivatives exhibit various activities including strong activities to control plant growth against various plants i.e. activities to shorten stems, to promote tillering, to control development of fresh buds, to promote development of flower buds or to thin fruits (or flowers), or in some cases, to promote formation of axillary buds, and yet they are capable of solving the problems of the conventional plant growth regulants. The present invention has been accomplished on the basis of these discoveries.

The present invention provides a benzamide derivative of the formula:

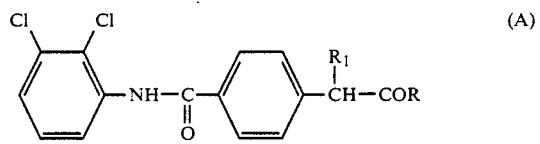
(A)

wherein $R_1$ is hydrogen or methyl, and R is hydroxyl, $C_1$-$C_6$ alkoxy, alkenylalkoxy, alkoxyalkoxy, amino, $C_1$-$C_4$ monoalkylamino, monoalkenylamino, dialkylamino or O-cat wherein cat is a metal, ammonium or an organic cation.

The benzamide derivative of the present invention is capable of reducing the difference in the activities against rice due to the variation in the dose, without substantially impairing the basic activities as the plant growth regulant as disclosed with respect to the phenoxy acetic acid (propionic acid) benzamide derivatives (Japanese Unexamined Patent Publications No. 216803/1988 and No. 29348/1989). Further, the sensitivities of wheat, barley, lawn grass of cold area type and egg plants are thereby improved, and their effects against these plants are excellent. Their activities in the horticultural field are also excellent, whereby application at a low concentration is now possible. The benzamide derivative of the present invention is therefore useful in a wide range of fields including dwarfing, induction of flower buds and thinning of fruits by properly selecting the time for the treatment. When the compound of the present invention is used as plant growth regulant, care should be taken so that it is applied sufficiently to the foliage of plants. The dose varies depending upon the type of the plant to be treated, the type of the compound or the time of application. However, it is usually applied at a dose of the active ingredient within a range of from 0.1 to 100 g/a (gram-/are), preferably from 1 to 50 g/a. It is common to employ the compound of the present invention in the form of various formulations including a wettable powder, an emulsifiable concentrate, a dust or a microgranule formulation.

As a lodging reducing agent, the active ingredient is applied at a dose within a range of from 0.5 to 4 g/a during a period ranging from 20 days prior to heading to the time of heading. To control lawn grasses, the active ingredient is applied at a dose within a range of from 5 to 20 g/a immediately prior to cutting.

To dwarf broad leaf gramineous plants or to prevent overgrowth thereof, the active ingredient is applied at a dose within a range of from 1 to 10 g/a during a period of from immediate prior to the growing period to the initial stage of the growing period. To dwarf green trees or to prevent spindly growth, the active ingredient is applied at a dose within a range of from 3 to 30 g/a immediately prior to trimming or at the time when new buds have grown to a few centimeter after trimming.

To induce flower buds or to promote development of flower buds, the active ingredient is applied at a dose within a range of from 0.2 to 2 g/a prior to the formation of flower buds. To thin fruits, the same dose is applied during one month from full bloom.

To control the flower stem development of root crops or to increase the sugar content of root crops, the active ingredient is applied at a dose within a range of from 5 to 20 g/a immediately prior to the flower stem development, or spot treatment is applied.

To improve the storage stability of root crops, the active ingredient is applied at a dose within a range of from 5 to 40 g/a from one to two weeks prior to hervest.

To increase the sugar content in sugar cane, the active ingredient is applied at a dose within a range of from 10 to 30 g/a from one week to two month prior to heading.

To control the height of large weeds in a non-agricultural field, the active ingredient is applied at a dose within a range of from 12.5 to 100 g/a when they have grown to a height from 30 to 100 cm, or when they have grown to a height exceeding 30 cm after cutting.

As an agent to prolong the life of cut flowers, flower bud portions are immersed in a solution containing from 5 to 50 ppm of the active ingredeint, followed by storage or use. Otherwise, a diluted solution is continuously permitted for absorption from the time of the flower buds.

Now, representative compounds of the present invention will be given in Table 1. The respective compounds will be identified by compound Nos.

TABLE 1

| Compound No. | Chemical formula | Melting point (°C.) |
|---|---|---|
| 1 | 2,3-Cl$_2$-C$_6$H$_3$-NH-C(=O)-C$_6$H$_4$-CH$_2$COOH | 184–185.5 |
| 2 | 2,3-Cl$_2$-C$_6$H$_3$-NH-C(=O)-C$_6$H$_4$-CH$_2$COOCH$_3$ | 102.5–103 |
| 3 | 2,3-Cl$_2$-C$_6$H$_3$-NH-C(=O)-C$_6$H$_4$-CH$_2$COOC$_2$H$_5$ | 96–97.5 |
| 4 | 2,3-Cl$_2$-C$_6$H$_3$-NH-C(=O)-C$_6$H$_4$-CH$_2$COOC$_3$H$_7$-n | 77.5–78 |
| 5 | 2,3-Cl$_2$-C$_6$H$_3$-NH-C(=O)-C$_6$H$_4$-CH$_2$COOC$_3$H$_7$-i | 89–90 |
| 6 | 2,3-Cl$_2$-C$_6$H$_3$-NH-C(=O)-C$_6$H$_4$-CH$_2$COOC$_4$H$_9$-n | 78.5–79 |

TABLE 1-continued

| Compound No. | Chemical formula | Melting point (°C.) |
|---|---|---|
| 7 | 2,3-Cl$_2$-C$_6$H$_3$-NH-CO-C$_6$H$_4$-CH$_2$COOCH$_2$CH=CH$_2$ | 83.5–84.5 |
| 8 | 2,3-Cl$_2$-C$_6$H$_3$-NH-CO-C$_6$H$_4$-CH$_2$COOC$_2$H$_4$OC$_4$H$_9$-n | 81.5–83 |
| 9 | 2,3-Cl$_2$-C$_6$H$_3$-NH-CO-C$_6$H$_4$-CH$_2$CONH$_2$ | 226–229 |
| 10 | 2,3-Cl$_2$-C$_6$H$_3$-NH-CO-C$_6$H$_4$-CH$_2$CONHCH$_3$ | 186–188 |
| 11 | 2,3-Cl$_2$-C$_6$H$_3$-NH-CO-C$_6$H$_4$-CH$_2$CONHC$_3$H$_7$-n | 177–178 |
| 12 | 2,3-Cl$_2$-C$_6$H$_3$-NH-CO-C$_6$H$_4$-CH$_2$CONHC$_3$H$_7$-i | 221–222 |
| 13 | 2,3-Cl$_2$-C$_6$H$_3$-NH-CO-C$_6$H$_4$-CH$_2$CONHCH$_2$CH=CH$_2$ | 174.5–175.5 |
| 14 | 2,3-Cl$_2$-C$_6$H$_3$-NH-CO-C$_6$H$_4$-CH$_2$CONHC$_4$H$_9$-n | 189–190 |
| 15 | 2,3-Cl$_2$-C$_6$H$_3$-NH-CO-C$_6$H$_4$-CH$_2$CONHC$_4$H$_9$-i | 187.5–188.5 |
| 16 | 2,3-Cl$_2$-C$_6$H$_3$-NH-CO-C$_6$H$_4$-CH$_2$CONHC$_4$H$_9$-sec | 217.5–218.5 |
| 17 | 2,3-Cl$_2$-C$_6$H$_3$-NH-CO-C$_6$H$_4$-CH$_2$CONHC$_4$H$_9$-t | 181.5–182 |

TABLE 1-continued

| Compound No. | Chemical formula | Melting point (°C.) |
|---|---|---|
| 18 | 2,3-Cl$_2$-C$_6$H$_3$-NH-C(=O)-C$_6$H$_4$-CH$_2$CON(C$_2$H$_5$)$_2$ | 133–135 |
| 19 | 2,3-Cl$_2$-C$_6$H$_3$-NH-C(=O)-C$_6$H$_4$-CH$_2$CON(C$_4$H$_9$-n)$_2$ | 106.5–107 |
| 20 | 2,3-Cl$_2$-C$_6$H$_3$-NH-C(=O)-C$_6$H$_4$-CH$_2$COONa | at least 230 |
| 21 | 2,3-Cl$_2$-C$_6$H$_3$-NH-C(=O)-C$_6$H$_4$-CH$_2$COOH·N(C$_2$H$_5$)$_3$ | 97–102 |
| 22 | 2,3-Cl$_2$-C$_6$H$_3$-NH-C(=O)-C$_6$H$_4$-CH(CH$_3$)COOH | 141–142 |
| 23 | 2,3-Cl$_2$-C$_6$H$_3$-NH-C(=O)-C$_6$H$_4$-CH(CH$_3$)COOC$_2$H$_5$ | 59–59.5 |
| 24 | 2,3-Cl$_2$-C$_6$H$_3$-NH-C(=O)-C$_6$H$_4$-CH(CH$_3$)COOC$_4$H$_9$-n | 60–61 |
| 25 | 2,3-Cl$_2$-C$_6$H$_3$-NH-C(=O)-C$_6$H$_4$-CH(CH$_3$)COOC$_4$H$_9$-i | 70–72 |
| 26 | 2,3-Cl$_2$-C$_6$H$_3$-NH-C(=O)-C$_6$H$_4$-CH(CH$_3$)COO-cyclohexyl | 48–51 |
| 27 | 2,3-Cl$_2$-C$_6$H$_3$-NH-C(=O)-C$_6$H$_4$-CH(CH$_3$)COOCH$_2$CH$_2$OC$_4$H$_9$-n | 62–63 |
| 28 | 2,3-Cl$_2$-C$_6$H$_3$-NH-C(=O)-C$_6$H$_4$-CH(CH$_3$)COONa | at least 200 |

TABLE 1-continued

| Compound No. | Chemical formula | Melting point (°C.) |
|---|---|---|
| 29 | 2,3-Cl₂-C₆H₃-NH-CO-C₆H₄-CH(CH₃)COOH·N(C₂H₅)₃ | 101-103 |
| 30 | 2,3-Cl₂-C₆H₃-NH-CO-C₆H₄-CH(CH₃)CONHCH₃ | 181-181.5 |
| 31 | 2,3-Cl₂-C₆H₃-NH-CO-C₆H₄-CH(CH₃)CONHC₃H₇-i | 203-204 |
| 32 | 2,3-Cl₂-C₆H₃-NH-CO-C₆H₄-CH(CH₃)CONHC₄H₉-t | 152-154 |
| 33 | 2,3-Cl₂-C₆H₃-NH-CO-C₆H₄-CH(CH₃)CONHCH₂CH=CH₂ | 173-175 |
| 34 | 2,3-Cl₂-C₆H₃-NH-CO-C₆H₄-CH(CH₃)CON(CH₃)₂ | 146-148 |
| 35 | 2,3-Cl₂-C₆H₃-NH-CO-C₆H₄-CH(CH₃)CON(C₂H₅)₂ | 119-120 |
| 40 (Comparative) | 2,3-Cl₂-C₆H₃-NH-CO-C₆H₄-OCH₂COOH | 198-199.5 |

The benzamide derivative of the present invention can readily be produced in good yield by reacting a compound of the formula:

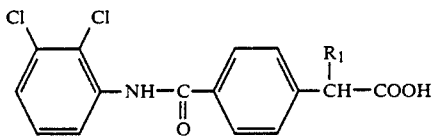

(I)

wherein $R_1$ is as defined above, with various alcohols, alkoxy alcohols, alkenyl alcohols, monoalkylamines, dialkylamines or alkenylamines in an organic solvent such as tetrahydrofuran, dioxane, methylene chloride or toluene by means of a dehydration condensing agent such as dicyclohexyl carbodiimide or N,N'-carbonyldiimidazol.

Further, the compound of the formula I can be reacted with various alcohols, alkoxy alcohols or alkenyl alcohols in an organic solvent such as benzene or toluene in the presence of concentrated sulfuric acid to form the corresponding benzamide derivatives.

A compound of the formula I wherein $R_1$ is hydrogen, can be prepared by the process as shown by the following formulas

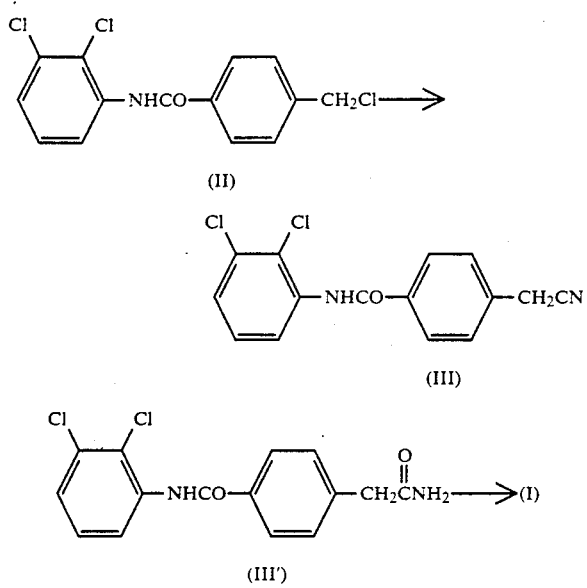

(II)

(III)

(III')

Namely, a compound of the formula II is reacted with an inorganic cyanide compound such as sodium cyanide or potassium cyanide in a polar solvent such as N,N-dimethylformamide or dimethylsulfoxide, to obtain a compound of the formula III. The compound of the formula III is hydrolyzed by 95% sulfuric acid to obtain an acid amide derivative of the formula III', which is then reacted with sodium nitrite in acetic acid in the presence of a sulfuric acid catalyst to obtain the compound of the formula I wherein $R_1$ is hydrogen.

A compound of the formula I wherein $R_1$ is methyl can be prepared by a process of the following formulas:

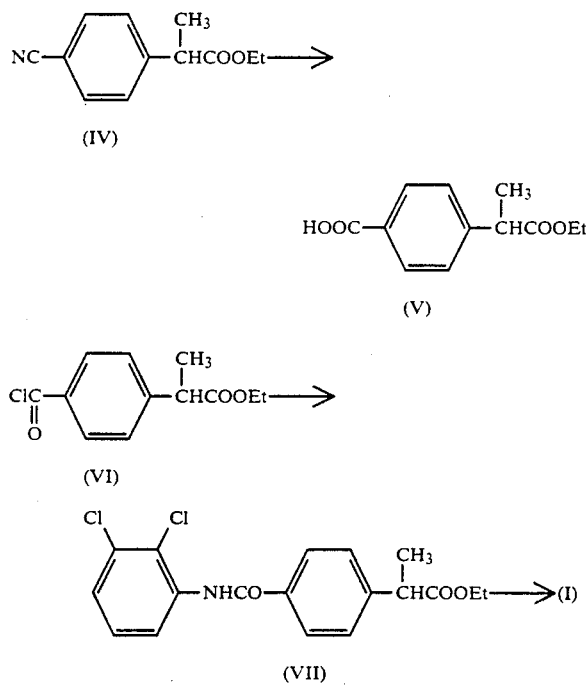

(IV)

(V)

(VI)

(VII)

Namely, a compound of the formula IV is hydrolyzed with 95% sulfuric acid to obtain an acid amide derivative, which is then reacted with sodium nitrite in acetic acid in the presence of a sulfuric acid catalyst to obtain a compound of the formula V. Then, the compound of the formula V is converted with e.g. thionyl chloride to an acid chloride derivative of the formula VI, which is then reacted with 2,3-dichloroaniline in an organic solvent such as acetone in the presence of a suitable acid acceptor such as sodiumhydrogen carbonate to obtain a compound of the formula VII. The compound of the formula VII is hydrolyzed with e.g. sodium hydroxide to obtain the compound of the formula I wherein $R_1$ is methyl.

Now, Examples of the preparation of representative compounds of the present invention will be described. However, it should be understood that the present invention is by no means restricted by such specific Examples.

EXAMPLE 1

Preparation of Compound No. 9 as identified in Table 1

30.2 g of 2',3'-dichloro-4-chloromethyl-benzanilide was dispersed in 200 ml of N,N-dimethylformamide, and 5.8 g of sodium cyanide was added thereto. The mixture was stirred at room temperature for 8 hours. After completion of the reaction, insoluble substances were removed by filtration. The filtrate was poured into 500 ml of water and extracted three times with 150 ml of ethyl acetate. The extract was washed twice with 200 ml of water and then dried over anhydrous magnesium sulfate. Then, the solvent was distilled off, and the residue was purified by silica gel chromatography (methylene chloride) to obtain a compound of the formula III. This compound was dissolved in 200 ml of 95% sulfuric acid, and the solution was stirred at room temperature for 7 hours. After completion of the reaction, the reaction solution was poured into 500 ml of ice water, and the resulting crystals were collected by filtration, washed with water and dried to obtain 23.5 g of desired 4-(2,3-dichlorophenylcarbamoyl)phenylacetamide. The yield was 76.7%, and the metling point of this compound was from 226° to 229° C.

EXAMPLE 2

Preparation of Compound No. 1 as identified in Table 1

10.7 g of 4-(2,3-dichlorophenylcarbamoyl)-phenylacetamide was dispersed in 100 ml of acetic acid, and 17.5 ml of sulfuric acid was added. Then, a solution obtained by dissolving 3.2 g of sodium nitrite in 17.5 ml of water, was dropwise added to bring the reaction temperature to a level of 20° C. ±5° C. Thereafter, the mixture was stirred at room temperature for two hours, and then poured into 400 ml of ice water. The resulting crystals are collected by filtration, thoroughly washed with water and then dried to obtain 9.8 g of desired 4(2,3-dichlorophenylcarbamoyl)phenyl acetic acid. The yield was 91.3%, and the melting point of this compound was from 184° to 185.5° C.

EXAMPLE 3

Preparation of Compound No. 8 as identified in Table 1

A mixture comprising 1.5 g of 4-(2,3-dichlorophenylcarbamoyl)phenyl acetic acid, 0.55 g of 2-n-butoxyethanol, 0.5 ml of concentrated sulfuric acid and 30 ml of toluene, was refluxed for 7 hours while removing water by a partial condenser. After completion of the reaction, 50 ml of ethyl acetate and 100 ml of water were added for extraction. The organic layer was washed with water and dried over anhydrous magnesium sulfate. The solvent was distilled off, and the residue was recrystallized from benzene-hexane to obtain 1.82 g of desired 2-n-butoxyethyl 4-(2,3-dichlorophenylcarbamoyl)phenyl acetate. The yield was 92.7%, and the melting point of this compound was from 81.5° to 83° C.

EXAMPLE 4

Preparation of Compound No. 11 as identified in Table 1

1.5 g of 4-(2,3-dichlorophenylcarbamoyl)phenyl acetic acid was dissolved in 30 ml of anhydrous tetrahydrofuran. While cooling the solution with ice water, 0.75 g of N,N'-carbonyldiimidazole was added thereto, and the mixture was stirred for 30 minutes. Thereafter, 0.27 g of n-propylamine was added thereto. The mixture was returned to room temperature and stirred for 5 hours. After completion of the reaction, the reaction solution was poured into 200 ml of water. The resulting crystals were collected by filtration, washed with water and dried, and then recrystallized from benzene-hexane to obtain 1.5 g of desired N-n-propyl-4-(2,3-dichlorophenylcarbamoyl)phenylacetamide. The yield was 88.8%, and the melting point of this compound was from 177° to 178° C.

EXAMPLE 5

Preparation of Compound No. 20 as identified in Table 1

1.5 g of 4-(2,3-dichlorophenylcarbamoyl)phenyl acetic acid was dissolved in 30 ml of methanol, and 0.2 g of sodium hydroxide was added thereto. The mixture was stirred for one hour. Insoluble substances were removed by filtration, and methanol was distilled off from the filtrate to obtain 1.49 g of desired sodium salt of 4(2,3-dichlorophenylcarbamoyl)phenyl acetic acid. The yield was 93.0 %, and the melting point of this compound was at least 230° C.

EXAMPLE 6

Preparation of Compound No. 23 as identified in Table 1 a) Preparation of a compound of the formula V 8.12 g of ethyl 2-(4-cyanophenyl)-propionate was dissolved in 50 ml of 95% sulfuric acid, and the solution was stirred at room temperature for 7 hours. The reaction solution was poured into 300 ml of ice water and extracted with 300 ml of ethyl acetate. The extract was washed sequentially with an aqueous sodiumhydrogen carbonate solution and with water and then dried over anhydrous magensium sulfate. Then, the solvent was distilled off to obtain the corresponding acid amide derivative. This derivative was dispersed in 100 ml of acetic acid, and 6 ml of sulfuric acid was added thereto. Then, a solution obtained by dissolving 7.46 g of sodium nitrite in 20 ml of water, was dropwise added to bring the reaction temperature to a level of 20° C. ±5° C. After completion of the dropwise addition, the mixture was stirred at from temperature for two hours. Then, the reaction solution was poured into 400 ml of ice water, and the resulting crystals were collected by filtration, thoroughly washed with water and then dried to obtain 6.8 g of the desired compound of the formula V. The yield was 76.6%.

b) Preparation of ethyl 2-[4-(2,3-dichlorophenylcarbamoyl)-phenyl]-propionate

A mixture comprising 6.66 g of the compound of the formula V, 5.35 g of thionyl chloride and 30 ml of dioxane, was stirred at 80° C. for 3 hours. Thereafter, the solvent and excess thionyl chloride was distilled off to obtain a compound of the formula VI which is an acid chloride derivative. To this compound, 20 ml of acetone and 5.04 g of sodium hydrogen carbonate were added. While stirring the mixture, a solution of 4.38 g of 2,3-dichloroaniline in 20 ml of acetone, was dropwise added over a period of 20 minutes at room temperature. The mixture was stirred at room temperature for 2 hours. Then, 100 ml of water and 200 ml of methylene chloride were added for extraction. The organic layer was washed with water and dried over anhydrous magnesium sulfate. Then, the solvent was distilled off, and the residue was recrystallized from toluene-hexane to obtain 9.3 g of desired ethyl 2-[4-(2,3-dichlorophenylcarbamoyl)-phenyl]propionate. The yield was 85%, and the melting point of this compound was from 59° to 59.5° C.

EXAMPLE 7

Preparation of Compound No. 22 as identified in Table 1

A mixture comprising 3.66 g of ethyl 2-[4-(2,3-dichlorophenylcarbomoyl)-phenyl]-propionate, 50 ml of methanol and 10 ml of a 2N-sodium hydroxide aqueous solution, was stirred at room temperature for 3 hours. Thereafter, the reaction solution was poured into 100 ml of ice water, and the pH was adjusted to 1 with concentrated hydrochloric acid. The resulting crystals were collected by filtration, thoroughly washed with water and dried to obtain 3.14 g of desired 2-[4-(2,3-dichlorophenylcarbamoyl)-phenyl]-propionic acid. The yield was 93%, and the melting point of this compound was from 141° to 142° C.

EXAMPLE 8

Preparation of Compound No. 25 as identified in Table 1

3.38 g of 2-[4-(2,3-dichlorophenylcarbamoyl)-phenyl]propionic acid was dissolved in 30 ml of anhydrous tetrahydrofuran. While cooling the solution with ice water, 2.43 g of N,N'-carbonyldiimidazole was added thereto, and the mixture was stirred for 30 minutes. Thereafter, 0.74 g of isobutyl alcohol was added thereto. The mixture was returned to room temperature and stirred for 5 hours. After completion of the reaction, the reaction solution was poured into 300 ml of water, and the resulting crystals were collected by filtration, washed with water and dried, and then recrystallized from toluene-hexane to obtain 3.15 g of desired isobutyl 2-[4-(2,3-dichloropheylcarbamoyl)-phenyl]-propionate. The yield was 80%, and the melting point of this compound was from 70° to 72° C.

EXAMPLE 9

Preparation of Compound No. 31 as identified in Table 1

3.38 g of 2-[4-(2,3-dichlorophenylcarbamoyl)phenyl]-propionic acid was dissolved in 30 ml of anhydrous tetrahydrofuran. While cooling the solution with ice water, 2.43 g of N,N'-carbonyldiimidazole was added thereto, and the mixture was stirred for 30 minutes. Thereafter, 0.59 g of isopropylamine was added thereto. The mixture was returned to room temperature and stirred for 5 hours. After completion of the reaction, the reaction solution was poured into 200 ml of water, and the resulting crystals were collected by filtration, washed with water and dried, and then recrystallized from toluene to obtain 3.30 g of desired N-isopropyl-2-[4-(2,3-dichlorophenylcarbamoyl)-phenyl]-propionamide. The yield was 87%, and the melting point of this compound was from 203° to 204° C.

Now, Formulation Examples will be given. In these Examples, "parts" means "parts by weight" unless otherwise specified.

FORMULATION EXAMPLE 1

Preparation of wettable powder (Compound No. 1)

To 40 parts of Compound No. 1, 49 parts of kaolin clay and 3 parts of white carbon were added, and the mixture was mixed and pulverized by a kneader. Then, powdery surfactants i.e. 2 parts of Rapizol BB-75 (trade mark, dialkyl sulfosuccinate 75%, manufactured by Nippon Oil and Fats Co., Ltd.) and 6 parts of Sorpol 5039 (trade mark, polyoxyethylene alkylarylether sulfate 50%, manufactured by Toho Kagaku K.K.) were mixed thereto to obtain a wettable powder containing 40% by weight of Compound No. 1.

FORMULATION EXAMPLE 2

Preparation of wettable powder (Compound No. 22)

In the same manner as in Formulation Example 1, a wettable powder containing 30% by weight of Compound No. 22 with the following composition was prepared.

| | |
|---|---|
| Compound No. 22 | 30 parts |
| Kaolin clay | 60 parts |
| White carbon | 2 parts |
| Rapizol BB-75 | 2 parts |
| Sorpol 5039 | 6 parts |

FORMULATION EXAMPLE 3

Preparation of emulsifiable concentrate (Compound No. 6)

10 Parts of Compound No. 6 was dissolved in 47 parts of xylene and 33% of cyclohexanone, and 10 parts of Sorpol 800A (a mixture of polyoxyethylene sorbitan alkylate, polyoxyethylene nonylphenyl ether and special anion) was added thereto and dissolved under stirring to obtain an emulsifiable concentrate containing 10% by weight of Compound No. 6.

FORMULATION EXAMPLE 4

Preparation of emulsifiable concentrate (Compound No. 26)

In the same manner as in Formulation Example 3, an emulsifiable concentrate containing 25% by weight of Compound No. 26 with the following composition was prepared.

| | |
|---|---|
| Compound No. 26 | 25 parts |
| Toluene | 35 parts |
| Cyclohexanone | 30 parts |
| Sorpol 800A | 10 parts |

FORMULATION EXAMPLE 5

Preparation of dust (Compound No. 10)

5 Parts of a wettable powder containing 40% by weight of Compound No. 10 prepared in the same manner as in Formulation Example 1 was thoroughly mixed with 0.3 parts of Rapizol BB-75 and 94.7 parts of clay to obtain a dust containing 2% by weight of Compound No. 10.

FORMULATION EXAMPLE 6

Preparation of dust (Compound No. 28)

In the same manner as in Formulation Example 5, a dust containing 1% by weight of Compound No. 28 with the following composition was prepared.

Wettable powder containing

| | |
|---|---|
| 20% by weight of Compound No. 28 | 5 parts |
| Rapizol BB-75 | 0.3 part |
| Clay | 94.7 parts |

FORMULATION EXAMPLE 7

Preparation of micro-granule formulation (Compound No. 2)

To 50 parts of Compound No. 2, 3 parts of white carbon and 47 parts of kaolin clay were mixed, and the mixture was pulverized. 4 Parts of the pulverized mixture was added to 94 parts of fine particulate zeolite (48-150 mesh) under stirring in a speed kneader. While continuing the stirring, 2 parts by weight of polyoxyethylene dodecylether diluted with water was poured thereto. The mixture was prepared with a small amount of water until no powder was observed, and the mixture was withdrawn and dried under air stream to obtain a micro-granule formulation containing 2% by weight of Compound No. 2.

FORMULATION EXAMPLE 8

Preparation formulation F (Compound No. 34)

In the same manner as in Formulation Example 7, a micro-granule formulation F containing 2% by weight of compound No. 34 with the following composition, was prepared.

| | |
|---|---|
| Compound No. 34 | 2 parts |
| White carbon | 1 part |
| Fine particulate zeolite (65-250 mesh) | 46 parts |
| Fine particulate calcium carbonate (65-250 mesh) | 50 parts |
| Dialkyl sulfosuccinate | 1 part |

FORMULATION EXAMPLE 9

Preparation of liquid formulation (Compound No. 21)

10 Parts of Compound No. 21 was dissolved in distilled water to obtain a liquid formulation containing 10% by weight of Compound No. 21.

FORMULATION EXAMPLE 10

Preparation of liquid formulation (Compound No. 22)

In the same manner as in Formulation Example 9, a liquid formulation with the following composition was prepared:

| | |
|---|---|
| Potassium salt of Compound No. 22 | 10 parts |
| Distilled water | 90 parts |

FORMULATION EXAMPLE 11

Preparation of flowable formulation (Compound No. 14)

To 40 parts of Compound No. 14, 50.3 parts of water, 5 parts of Sorpol 3742 (trade mark, polyoxyethylene styrylphenyl ether sulfate, manufactured by Toho Kagaku K.K.) as a surfactant and 0.5 part of Sorpol 7512 as a defoamer (a silicone type defoamer), were added, and the mixture was pulverized by a sand grinder. After taking the mixture out, 4 parts of ethylene glycol and 0.2 part of Vangel-B (trademark, an inorganic thickner containing Mg, Al and Si, manufactured by Sanyo Kasei K.K.) were added as a thickener and stabilizer, and the mixture was thoroughly stirred to obtain a flowable formulation containing 40% by weight of Compound No. 14.

FORMULATION EXAMPLE 12

Preparation of flowable formulation (Compound No. 32)

In the same manner as in Formulation Example 11, a flowable formulation containing 40% by weight of Compound No. 32 with the following composition was prepared.

| | |
|---|---|
| Compound No. 32 | 40 parts |
| Water | 50.3 parts |
| Sorpol 3742 | 5 parts |
| Sorpol 7512 | 0.5 part |
| Ethylene glycol | 4.0 parts |
| Vangel-B | 0.2 parts |

TEST EXAMPLE 1

Foliar treatment tests on various plants (plant growth regulant)

Rice (*Oryza sativa*) (Or), wheat (*Triticum aestivaum*) (Tr), French bean (*Phaseolus vulgaris* L.) (Ph) having vines, lettuce (Le) and tomato (To) were separately grown in porous pots of 60 cm$^2$, and thinned depending upon the size of the plants. The growth degrees were adjusted to a level of 3.5 leaf stage, and a diluted solution of each test compound was applied to the foliage of the plants by using a spray gan in an amount of 10 liter/a. 30 days later, the growth inhibition was evaluated. The results are shown in Table 2.

The evaluation was made in accordance with the following standards:

Growth control effects

0: Same as no treatment
1: Growth inhibition of about 20% as compared with no treatment
2: Growth inhibition of about 40% as compared with no treatment
3: Growth inhibition of about 60% as compared with no treatment
4: Growth inhibition of about 80% as compared with no treatment
5: No progress in growth observed since the treatment Activities G: Deepening of green color of leaves
T: Tillering
M: Malformed leaves
B: Withering of leaves

TABLE 2

Results of foliar treatment tests on various plants

| Compound No. | Concentration of active ingredient (%) | Growth control effects | | | | |
|---|---|---|---|---|---|---|
| | | Or | Tr | Ph | Le | To |
| 1 | 0.1 | 5 | 5 | 5G | 5 | 4 |
| | 0.05 | 4T | 4.5T | 4 | 4 | 3 |
| | 0.025 | 3 | 4T | 3 | 3 | 2 |
| 3 | 0.1 | 5 | 5 | 5G | 5G | 4.5 |
| | 0.05 | 5T | 5T | 4.5 | 5 | 4 |
| | 0.025 | 4T | 4T | 4 | 4 | 3 |
| 5 | 0.1 | 5 | 5 | 5B | 5G | 5 |
| | 0.05 | 5T | 5 | 5G | 5 | 4 |
| | 0.025 | 4.5T | 5T | 4.5 | 5 | 3 |
| 8 | 0.1 | 5 | 5 | 5G | 5G | 5 |
| | 0.05 | 5T | 5 | 5G | 5G | 4 |
| | 0.025 | 4.5T | 5T | 4.5 | 5 | 3 |
| 9 | 0.1 | 5T | 5 | 5 | 5 | 4 |
| | 0.05 | 4 | 4.5T | 4 | 4 | 3 |
| | 0.025 | 3 | 3 | 3 | 3 | 2 |
| 11 | 0.1 | 5 | 5 | 5 | 5G | 4.5 |
| | 0.05 | 5T | 5T | 4 | 5 | 4 |
| | 0.025 | 4T | 4T | 3 | 4 | 3 |
| 15 | 0.1 | 5 | 5 | 5B | 5G | 4 |
| | 0.05 | 5T | 5T | 5G | 5 | 3 |
| | 0.025 | 4T | 4T | 4 | 4 | 2 |
| 17 | 0.1 | 5 | 5 | 5G | 5 | 4 |
| | 0.05 | 5T | 5T | 4.5 | 5 | 3 |
| | 0.025 | 4T | 4T | 4 | 4 | 2 |
| 19 | 0.1 | 5 | 5 | 5G | 5 | 3 |
| | 0.05 | 4T | 4T | 4.5 | 4 | 2 |
| | 0.025 | 3 | 3 | 4 | 3 | 1 |
| 20 | 0.1 | 5 | 5 | 5 | 5 | 4 |
| | 0.05 | 4 | 4.5T | 4 | 4 | 3 |
| | 0.025 | 3 | 4T | 3 | 3 | 2 |
| 22 | 0.1 | 5 | 5 | 5B | 5 | 4 |
| | 0.05 | 5 | 5 | 5G | 4 | 3 |
| | 0.025 | 4.5T | 5T | 4 | 3 | 2 |
| 23 | 0.1 | 5 | 5 | 5G | 5G | 5 |
| | 0.05 | 5T | 5 | 5 | 4.5 | 4 |
| | 0.025 | 4.5T | 4T | 4 | 4 | 3 |
| 25 | 0.1 | 5 | 5 | 5G | 5 | 4 |
| | 0.05 | 4.5T | 4.5T | 4 | 4 | 3 |
| | 0.025 | 4T | 4T | 3 | 3 | 2 |
| 27 | 0.1 | 5 | 5 | 5G | 5 | 4 |
| | 0.05 | 4T | 4.5T | 4 | 4 | 3 |
| | 0.025 | 4T | 4T | 3 | 3 | 2 |
| 28 | 0.1 | 5 | 5 | 5G | 5 | 4 |
| | 0.05 | 5T | 5 | 4.5 | 4.5 | 3 |
| | 0.025 | 4T | 4T | 4 | 4 | 2 |
| 29 | 0.1 | 5 | 5 | 5B | 5 | 4 |
| | 0.05 | 5 | 5 | 5G | 4 | 3 |
| | 0.025 | 4T | 4T | 4 | 3 | 2 |
| 31 | 0.1 | 5 | 5 | 5G | 5 | 4 |
| | 0.05 | 4 | 4.5 | 4.5 | 4 | 3 |
| | 0.025 | 4T | 4T | 4 | 3 | 2 |
| 33 | 0.1 | 5 | 5 | 5G | 5 | 4 |
| | 0.05 | 4T | 4T | 4 | 4 | 3 |
| | 0.025 | 3 | 3 | 3 | 3 | 2 |
| 35 | 0.1 | 5 | 5 | 5G | 5 | 5 |
| | 0.05 | 4T | 4.5T | 4 | 4 | 4 |
| | 0.025 | 3 | 4 | 3 | 3 | 3 |
| 40 (Comparative) | 0.1 | 5 | 5 | 5 | 5 | 3 |
| | 0.05 | 4T | 4T | 3 | 4 | 1 |
| | 0.025 | 2 | 2 | 1 | 1 | 0 |

TEST EXAMPLE 2

Lodging reducing test on rice (treatment prior to heading)

A paddy field to which paddy field rice seedlings (Koshihikari) were transplanted by a transplanter in a usual manner, was divided into unit plots of 20 m². A wettable powder, an emulsifiable concentrate and a flowable formulation were diluted with water in an amount corresponding to 5 l/a (are) and uniformly sprayed to the respective unit plots by a hand sprayer. A dust, a micro-granule formulation (48-150 mesh) and a microgranule formulation F (65-250 mesh) were uniformly applied to the unit plots by a small duster.

The treatment was conducted twice i.e. 20 days and 7 days prior to heading of rice. At the harvest, the stem length and the panicle length were measured with respect to the longest stems of 15 plants in each unit plot, and the means value was computed. The yield was indicated as a mean value of the weights of brown rice reaped from two areas of 3.3 m² in each unit plot. The lodging degree was evaluated in accordance with the following standards:

0: No lodging
1: 20% lodging or slanting
2: 40% lodging or slanting
3: 60% lodging or slanting
4: 80% lodging or slanting
5: complete lodging The results are shown in Table 3. The numerical values represent percentages relative to the non-treated plots, which are indicated by rounding off to decimal place. The numerical values in the brackets ( ) in Table 3 are the actually measured values.

TABLE 3

| | | | Results of lodging reducing test on rice | | | | | | | |
|---|---|---|---|---|---|---|---|---|---|---|
| | | | 20 days prior to heading | | | | 7 days prior to heading | | | |
| Compound No. | Formulation type Content (%) | Dose of active ingredient (g/a) | Stem length (%) | Panicle length (%) | Yield (%) | Lodging degree | Stem length (%) | Panicle length (%) | Yield (%) | Lodging degree |
| 1 | Dust | 2.0 | 83 | 102 | 107 | 1 | 79 | 103 | 108 | 0 |
| | 0.5 | 1.0 | 89 | 103 | 110 | 1.5 | 85 | 105 | 107 | 1 |
| | | 0.5 | 94 | 99 | 106 | 2 | 90 | 101 | 102 | 1.5 |
| 3 | Wettable powder 30 | 2.0 | 78 | 98 | 108 | 0 | 73 | 99 | 105 | 0 |
| | | 1.0 | 82 | 104 | 111 | 0 | 78 | 98 | 106 | 0 |
| | | 0.5 | 89 | 101 | 103 | 1.5 | 83 | 102 | 108 | 1 |
| 4 | Emulsifiable concentrate 25 | 2.0 | 73 | 100 | 106 | 0 | 69 | 98 | 107 | 0 |
| | | 1.0 | 79 | 102 | 108 | 0 | 74 | 100 | 111 | 0 |
| | | 0.5 | 88 | 103 | 105 | 1 | 79 | 104 | 112 | 0 |
| 6 | Emulsifiable concentrate 25 | 2.0 | 75 | 99 | 108 | 0 | 70 | 99 | 110 | 0 |
| | | 1.0 | 80 | 102 | 107 | 0 | 76 | 97 | 108 | 0 |
| | | 0.5 | 85 | 101 | 110 | 1 | 81 | 103 | 109 | 0 |
| 8 | Flowable 20 | 2.0 | 73 | 103 | 108 | 0 | 70 | 101 | 106 | 0 |
| | | 1.0 | 81 | 104 | 106 | 0 | 77 | 106 | 104 | 0 |
| | | 0.5 | 86 | 101 | 104 | 1 | 83 | 104 | 109 | 1 |
| 9 | Wettable powder 50 | 2.0 | 82 | 99 | 108 | 0 | 80 | 103 | 108 | 0 |
| | | 1.0 | 89 | 101 | 105 | 1.5 | 86 | 106 | 110 | 1 |
| | | 0.5 | 96 | 100 | 103 | 3 | 91 | 101 | 103 | 2 |
| 13 | Microgranule formulation 0.5 | 4.0 | 85 | 105 | 107 | 1 | 81 | 98 | 111 | 0 |
| | | 2.0 | 90 | 102 | 105 | 2 | 87 | 102 | 108 | 1 |
| | | 1.0 | 96 | 107 | 104 | 3 | 92 | 101 | 104 | 2 |
| 18 | Flowable 25 | 2.0 | 86 | 107 | 110 | 1 | 82 | 99 | 109 | 0 |
| | | 1.0 | 92 | 101 | 105 | 2 | 88 | 101 | 107 | 1 |
| | | 0.5 | 97 | 99 | 103 | 3 | 92 | 99 | 110 | 2 |
| 20 | Microgranule formulation F 0.5 | 4.0 | 81 | 97 | 108 | 0 | 78 | 101 | 105 | 0 |
| | | 2.0 | 87 | 98 | 110 | 1 | 84 | 98 | 109 | 0 |
| | | 1.0 | 92 | 104 | 103 | 2 | 87 | 102 | 112 | 1 |
| 21 | Liquid formulation 10 | 2.0 | 77 | 97 | 106 | 0 | 72 | 103 | 107 | 0 |
| | | 1.0 | 82 | 98 | 108 | 0 | 77 | 99 | 112 | 0 |
| | | 0.5 | 88 | 101 | 105 | 1 | 81 | 102 | 104 | 0 |
| 22 | Wettable powder 50 | 2.0 | 71 | 99 | 108 | 0 | 69 | 99 | 105 | 0 |
| | | 1.0 | 80 | 102 | 110 | 0 | 73 | 103 | 108 | 0 |
| | | 0.5 | 83 | 103 | 107 | 1 | 79 | 101 | 105 | 0 |
| 23 | Emulsifiable concentrate 25 | 2.0 | 70 | 101 | 107 | 0 | 67 | 100 | 102 | 0 |
| | | 1.0 | 78 | 98 | 108 | 0 | 70 | 102 | 108 | 0 |
| | | 0.5 | 82 | 100 | 111 | 1 | 78 | 101 | 109 | 0 |
| 24 | Emulsifiable concentrate 25 | 2.0 | 76 | 100 | 108 | 0 | 71 | 103 | 104 | 0 |
| | | 1.0 | 79 | 103 | 110 | 0 | 75 | 101 | 106 | 0 |
| | | 0.5 | 83 | 104 | 111 | 1 | 80 | 101 | 109 | 0 |
| 28 | Microgranule formulation 0.5 | 4.0 | 88 | 101 | 108 | 1 | 84 | 97 | 108 | 1 |
| | | 2.0 | 93 | 98 | 105 | 2 | 88 | 102 | 105 | 1 |
| | | 1.0 | 96 | 102 | 103 | 2.5 | 92 | 101 | 104 | 2 |
| 29 | Dust | 2.0 | 87 | 98 | 110 | 1 | 81 | 100 | 108 | 0 |
| | 0.5 | 1.0 | 89 | 103 | 108 | 1.5 | 85 | 99 | 110 | 1 |
| | | 0.5 | 93 | 99 | 105 | 2 | 90 | 101 | 106 | 1.5 |
| 30 | Liquid formulation 15 | 2.0 | 77 | 102 | 106 | 0 | 71 | 101 | 105 | 0 |
| | | 1.0 | 79 | 103 | 106 | 0 | 75 | 104 | 107 | 0 |
| | | 0.5 | 84 | 99 | 109 | 1 | 79 | 101 | 110 | 0 |

TABLE 3-continued

| Compound No. | Formulation type Content (%) | Dose of active ingredient (g/a) | Results of lodging reducing test on rice | | | | | | | |
|---|---|---|---|---|---|---|---|---|---|---|
| | | | 20 days prior to heading | | | | 7 days prior to heading | | | |
| | | | Stem length (%) | Panicle length (%) | Yield (%) | Lodging degree | Stem length (%) | Panicle length (%) | Yield (%) | Lodging degree |
| 31 | Flowable 25 | 2.0 | 76 | 101 | 104 | 0 | 71 | 102 | 105 | 0 |
| | | 1.0 | 80 | 102 | 109 | 0 | 75 | 101 | 105 | 0 |
| | | 0.5 | 83 | 102 | 108 | 1 | 81 | 101 | 109 | 1 |
| 34 | Microgranule formulation F | 4.0 | 87 | 103 | 106 | 1 | 80 | 97 | 109 | 0 |
| | | 2.0 | 90 | 101 | 108 | 1 | 85 | 101 | 108 | 1 |
| | | 1.0 | 93 | 99 | 104 | 2 | 90 | 101 | 107 | 2 |
| | | 0.5 | | | | | | | | |
| 40 (Comparative) | Wettable powder 40 | 2.0 | 80 | 101 | 104 | 0 | 75 | 96 | 105 | 0 |
| | | 1.0 | 89 | 97 | 106 | 1.5 | 83 | 101 | 106 | 1 |
| | | 0.5 | 97 | 99 | 103 | 3 | 90 | 97 | 103 | 2 |
| No treatment | — | — | 100 | 100 | 100 | 4.5 | 100 (83.5 cm) | 100 (18.5 cm) | 100 (58.5 kg/a) | 4.5 |

TEST EXAMPLE 3

Lodging reducing test on wheat (treatment prior to heading)

A field of wheat (Norin No. 61) sown in rows in early November, was divided into unit plots of 20 m². Each compound diluted to a predetermined concentration was uniformly sprayed over the entire surface in a unit plot in an amount corresponding to 5 l/a on 20 days prior to heading i.e. early April and on 10 days prior to heading i.e. late April by a hand sprayer.

At the harvest in late June, the stem length and the panicle length were measured with respect to the longest stems of 15 plants of average growth, and the mean value was computed. The grain weight indicated is a mean value of the grain weights reaped from two areas of 3.3 m² in each unit plot. The lodging degree was evaluated by the same standards as in Test Example 2. The results are shown in Table 4.

The numerical values represent percentage values relative to the non-treated area, and the values in the brackets ( ) are the actually measured values.

TABLE 4

| Compound No. | Formulation type Content (%) | Dose of active ingredient (g/a) | Results of lodging reducing test on wheat | | | | | | | |
|---|---|---|---|---|---|---|---|---|---|---|
| | | | 20 days prior to heading | | | | 10 days prior to heading | | | |
| | | | Stem length (%) | Panicle length (%) | Grain weight (%) | Lodging degree | Stem length (%) | Panicle length (%) | Grain weight (%) | Lodging degree |
| 2 | Wettable powder 30 | 4.0 | 87 | 102 | 106 | 0 | 85 | 99 | 106 | 0 |
| | | 2.0 | 92 | 99 | 108 | 1 | 90 | 101 | 111 | 1 |
| | | 1.0 | 97 | 98 | 104 | 3 | 95 | 103 | 106 | 3 |
| 3 | Wettable powder 30 | 4.0 | 85 | 101 | 108 | 0 | 83 | 104 | 108 | 0 |
| | | 2.0 | 90 | 98 | 110 | 1 | 88 | 98 | 110 | 1 |
| | | 1.0 | 94 | 103 | 103 | 2 | 92 | 102 | 105 | 2 |
| 5 | Flowable 20 | 4.0 | 84 | 98 | 112 | 0 | 81 | 103 | 108 | 0 |
| | | 2.0 | 89 | 104 | 108 | 1 | 86 | 105 | 107 | 0 |
| | | 1.0 | 93 | 101 | 106 | 2 | 91 | 99 | 104 | 1 |
| 7 | Flowable 20 | 4.0 | 85 | 107 | 107 | 0 | 84 | 105 | 111 | 0 |
| | | 2.0 | 91 | 104 | 104 | 1 | 90 | 98 | 108 | 1 |
| | | 1.0 | 96 | 98 | 106 | 3 | 94 | 102 | 103 | 3 |
| 8 | Emulsifiable concentrate 20 | 4.0 | 82 | 106 | 109 | 0 | 80 | 98 | 110 | 0 |
| | | 2.0 | 87 | 102 | 105 | 0 | 86 | 99 | 107 | 0 |
| | | 1.0 | 93 | 105 | 108 | 2 | 91 | 104 | 108 | 1 |
| 10 | Wettable powder 50 | 4.0 | 88 | 101 | 107 | 1 | 87 | 101 | 106 | 0 |
| | | 2.0 | 92 | 104 | 110 | 1.5 | 91 | 97 | 112 | 1 |
| | | 1.0 | 98 | 99 | 102 | 4 | 97 | 98 | 104 | 3 |
| 15 | Wettable powder 50 | 4.0 | 86 | 106 | 106 | 0 | 84 | 102 | 109 | 0 |
| | | 2.0 | 90 | 96 | 112 | 1 | 88 | 98 | 108 | 1 |
| | | 1.0 | 94 | 101 | 104 | 2 | 92 | 104 | 105 | 2 |
| 19 | Wettable powder 30 | 4.0 | 87 | 102 | 105 | 1 | 85 | 99 | 108 | 0 |
| | | 2.0 | 91 | 97 | 107 | 1 | 88 | 105 | 107 | 1 |
| | | 1.0 | 96 | 98 | 103 | 3 | 93 | 101 | 105 | 2 |
| 20 | Flowable 25 | 4.0 | 86 | 105 | 106 | 0 | 84 | 98 | 107 | 0 |
| | | 2.0 | 89 | 96 | 108 | 1 | 88 | 107 | 108 | 1 |
| | | 1.0 | 95 | 101 | 106 | 3 | 94 | 101 | 106 | 3 |
| 21 | Liquid formulation 10 | 4.0 | 84 | 98 | 105 | 0 | 82 | 108 | 109 | 0 |
| | | 2.0 | 88 | 104 | 110 | 1 | 85 | 99 | 114 | 0 |
| | | 1.0 | 94 | 102 | 105 | 2 | 92 | 103 | 103 | 2 |
| 22 | Flowable 30 | 4.0 | 79 | 99 | 105 | 0 | 78 | 96 | 103 | 0 |
| | | 2.0 | 85 | 98 | 108 | 0 | 84 | 104 | 106 | 0 |
| | | 1.0 | 92 | 102 | 106 | 2 | 90 | 101 | 107 | 1 |
| 23 | Emulsifiable concentrate 25 | 4.0 | 77 | 104 | 104 | 0 | 75 | 100 | 103 | 0 |
| | | 2.0 | 83 | 99 | 109 | 0 | 82 | 95 | 107 | 0 |
| | | 1.0 | 90 | 101 | 104 | 2 | 89 | 104 | 109 | 2 |
| 25 | Emulsifiable | 4.0 | 84 | 103 | 107 | 0 | 82 | 98 | 107 | 0 |
| | | 2.0 | 90 | 100 | 105 | 1 | 87 | 102 | 108 | 0 |

TABLE 4-continued

| Compound No. | Formulation type Content (%) | Dose of active ingredient (g/a) | Results of lodging reducing test on wheat | | | | | | | |
|---|---|---|---|---|---|---|---|---|---|---|
| | | | 20 days prior to heading | | | | 10 days prior to heading | | | |
| | | | Stem length (%) | Panicle length (%) | Grain weight (%) | Lodging degree | Stem length (%) | Panicle length (%) | Grain weight (%) | Lodging degree |
| | concentrate 20 | 1.0 | 95 | 101 | 106 | 2 | 93 | 96 | 106 | 2 |
| 27 | Wettable powder 30 | 4.0 | 85 | 98 | 109 | 0 | 83 | 103 | 107 | 0 |
| | | 2.0 | 92 | 102 | 107 | 1 | 90 | 101 | 108 | 1 |
| | | 1.0 | 96 | 101 | 104 | 3 | 94 | 100 | 108 | 2 |
| 28 | Emulsifiable concentrate 30 | 4.0 | 78 | 97 | 103 | 0 | 77 | 102 | 104 | 0 |
| | | 2.0 | 83 | 105 | 105 | 0 | 82 | 104 | 107 | 0 |
| | | 1.0 | 88 | 96 | 108 | 1 | 91 | 102 | 106 | 1 |
| 30 | Wettable powder 30 | 4.0 | 81 | 101 | 107 | 0 | 80 | 102 | 105 | 0 |
| | | 2.0 | 85 | 97 | 107 | 0 | 85 | 98 | 108 | 0 |
| | | 1.0 | 92 | 102 | 105 | 2 | 91 | 99 | 107 | 1 |
| 33 | Flowable 30 | 4.0 | 87 | 103 | 106 | 0 | 85 | 101 | 106 | 0 |
| | | 2.0 | 93 | 99 | 107 | 2 | 91 | 97 | 108 | 1 |
| | | 1.0 | 99 | 98 | 101 | 4 | 97 | 98 | 102 | 3 |
| 35 | Wettable powder 50 | 4.0 | 86 | 103 | 109 | 0 | 84 | 104 | 107 | 0 |
| | | 2.0 | 92 | 98 | 106 | 1 | 90 | 101 | 107 | 1 |
| | | 1.0 | 98 | 101 | 102 | 4 | 96 | 106 | 103 | 3 |
| 40 (Comparative) | Wettable powder 40 | 4.0 | 87 | 98 | 107 | 1 | 88 | 103 | 106 | 1 |
| | | 2.0 | 95 | 102 | 105 | 3 | 93 | 108 | 106 | 2 |
| | | 1.0 | 99 | 100 | 102 | 4 | 98 | 99 | 102 | 4 |
| No treatment | — | — | 100 | 100 | 100 | 4.5 | 100 (86.7 cm) | 100 (9.7 cm) | 100 (47.4 kg/a) | 4.5 |

TEST EXAMPLE 4

Foliar treatment test on lawn

A tarf field of each of bent grass (Be), bluegrass (Bl), tall fescue (*Festuca arundinacea*) (Fe) and Zoysia (*Zoysia matrella*) (Zo) was divided into unit plots 2.25 m². Five days after mowing in a height of 25 mm, 5.0 ml of a diluted solution of each compound was uniformly applied to each plot by means of a hand sprayer. Three weeks after the application, the evaluation was conducted by the same evaluation standards as used in Test Example 1.

The change in the color of leaves was evaluated under the following standards:

| Color of leaves | | |
|---|---|---|
| Withering: | Slight | B-1 |
| | Little | B-2 |
| | Substantial | B-3 |
| Deepening: | Slight | G-1 |
| | Little | G-2 |
| | Substantial | G-3 |
| Densification: | Slightly high | D-1 |
| | Substantially high | D-2 |
| | Very high | D-3 |

The results are shown in Table 5.

TABLE 5

| Compound No. | Dose of active ingredient (g/a) | Results of foliar treatment on lawn | | | |
|---|---|---|---|---|---|
| | | Be | Bl | Fe | Zo |
| 1 | 20 | 4 | 4 | 4.5 G-1 | 4 D-1 |
| | 10 | 3 | 3 | 4 | 3 |
| | 5 | 2 | 2 | 3 | 2 |
| 3 | 20 | 4.5 G-2 | 4 | 4.5 G-2 | 4 D-1 |
| | 10 | 4 | 3 | 4 | 3 |
| | 5 | 3 | 2 | 3 | 2 |
| 5 | 20 | 4.5 G-1 | 4.5 G-2 | 4.5 G-1 | 4.5 G-2 |
| | 10 | 4 | 4 | 4 | 4 |
| | 5 | 3 | 3 | 3 | 3 |
| 8 | 20 | 4.5 G-1 | 4.5 G-2 | 4.5 G-2 | 4.5 G-2 |
| | 10 | 4 | 4 | 4 | 4 |
| | 5 | 3 | 3 | 3 | 3 |
| 11 | 20 | 4.5 D-2 | 4 | 4.5 G-1 | 4.5 G-1 |
| | 10 | 4 | 3 | 4 | 4 |
| | 5 | 3 | 2 | 3 | 3 |
| 14 | 20 | 4 D-1 | 4 | 4 D-1 | 4 D-1 |
| | 10 | 3 | 3 | 3 | 3 |
| | 5 | 2 | 2 | 2 | 2 |
| 16 | 20 | 4 | 4 | 4 D-1 | 4 |
| | 10 | 3 | 3 | 3 | 3 |
| | 5 | 2 | 2 | 2 | 2 |
| 20 | 20 | 4 D-1 | 4 | 4.5 G-1 | 4 D-1 |
| | 10 | 3 | 3 | 4 | 3 |
| | 5 | 2 | 2 | 3 | 2 |
| 22 | 20 | 4.5 G-3 | 4.5 G-2 | 4.5 G-2 | 4.5 G-2 |
| | 10 | 4 D-2 | 4 D-1 | 4 D-2 | 4 |
| | 5 | 3 | 3 | 3 | 3 |
| 24 | 20 | 4.5 G-2 | 4 | 4.5 G-2 | 4 D-1 |
| | 10 | 3 | 3 | 3 | 3 |
| | 5 | 2 | 2 | 2 | 2 |
| 26 | 20 | 4 D-2 | 3 | 4 D-1 | 4 D-1 |
| | 10 | 3 | 2 | 3 | 3 |
| | 5 | 1 | 1 | 1 | 2 |
| 28 | 20 | 4.5 G-3 | 4.5 G-2 | 4.5 G-2 | 4.5 G-1 |
| | 10 | 4 D-2 | 4 | 4 | 4 |
| | 5 | 3 | 2 | 3 | 3 |
| 29 | 20 | 4.5 D-1 | 4 | 4.5 G-2 | 4.5 G-2 |
| | 10 | 4 | 3 | 4 | 4 |
| | 5 | 2 | 2 | 2 | 3 |
| 30 | 20 | 4.5 D-2 | 4.5 | 4.5 G-2 | 4.5 G-2 |
| | 10 | 4 | 4 | 4 | 4 |
| | 5 | 2 | 2 | 3 | 3 |
| 32 | 20 | 4 D-1 | 3 | 4 D-1 | 4 |
| | 10 | 3 | 2 | 3 | 3 |
| | 5 | 2 | 1 | 2 | 2 |
| 40 (Comparative) | 20 | 2 | 2 | 3 | 2 |
| | 10 | 1 | 1 | 2 | 1 |
| | 5 | 0 | 0 | 1 | 0 |

TEST EXAMPLE 5

Dwarfing tests on various green trees

Seedlings of various green trees grown in a 200 cm² pot, which were nearly in the same growth degree, were selected. At the elongation period of fresh buds i.e. at spring, a diluted solution of each compound was sprayed in an amount corresponding to 10 l/a to the seedlings by a hand sprayer. Two weeks later, the phytotoxicity responses such as withering of leaves were evaluated, and the evaluation of the growth control and other responses were conducted three months later. The growth control effects were evaluated in accordance with the same standards as in Test Example 1. The results are shown in Table 6.

With respect to the heights test plants at the time of spraying, azelea (*Rhododendron indicum*) (Rh) and box tree (*Buxus microphylla*) (Bu) had a height of from 25 to 30 cm, and Chinese hawthorn (*Photinia glabra*) (Ph) and *Juniperus chinensis* (Ju), had a height of from 35 to 40 cm.

| Phytotoxicity | | |
|---|---|---|
| Withering of leaves: | Slight | B-1 |
| | Little | B-2 |
| | Substantial | B-3 |
| Whitening or yellowing: | Slight | C-1 |
| | Little | C-2 |
| | Substantial | C-3 |
| Other responses | | |
| Deepening: | Slight | G-1 |
| | Little | G-2 |
| | Substantial | G-3 |

TABLE 6

Dwarfing tests on various green trees

| Compound No. | Concentration of active ingredient (%) | Rh | Bu | Ph | Ju |
|---|---|---|---|---|---|
| 1 | 0.3 | 5 | 4.5 | 5 | 4 |
| | 0.1 | 4.5 | 4 | 4.5 | 3.5 |
| | 0.03 | 3 | 3 | 3 | 2 |
| 3 | 0.3 | 5 | 4.5 | 5 | 4 |
| | 0.1 | 4.5 | 4 | 4.5 | 3 |
| | 0.03 | 4 | 3 | 4 | 2 |
| 4 | 0.3 | 5 B-1 | 5 C-1 | 5 B-1 | 5 G-2 |
| | 0.1 | 5 G-2 | 4.5 | 5 | 4.5 |
| | 0.03 | 4 | 4 | 4 | 4 |
| 6 | 0.3 | 5 B-1 | 5 C-1 | 5 B-1 | 5 G-1 |
| | 0.1 | 5 | 5 | 5 | 4.5 |
| | 0.03 | 4 | 4 | 4 | 4 |
| 8 | 0.3 | 5 B-1 | 5 | 5 B-1 | 5 G-1 |
| | 0.1 | 5 G-1 | 5 | 5 G-1 | 4.5 |
| | 0.03 | 4 | 4 | 4 | 3 |
| 12 | 0.3 | 5 B-1 | 5 | 5 B-1 | 5 G-1 |
| | 0.1 | 4.5 | 4.5 | 4.5 | 4 |
| | 0.03 | 4 | 4 | 4 | 3 |
| 17 | 0.3 | 5 | 4.5 | 4.5 | 4 |
| | 0.1 | 4.5 | 4 | 4 | 3 |
| | 0.03 | 3 | 3 | 3 | 2 |
| 21 | 0.3 | 5 | 4.5 | 5 | 4 |
| | 0.1 | 4.5 | 4 | 4.5 | 3 |
| | 0.03 | 3 | 3 | 3 | 2 |
| 22 | 0.3 | 5 B-1 | 5 C-1 | 5 B-1 | 5 B-1 |
| | 0.1 | 5 G-2 | 5 G-2 | 5 G-1 | 4.5 |
| | 0.03 | 4 | 4 | 4 | 3 |
| 23 | 0.3 | 5 B-1 | 5 G-2 | 5 G-2 | 5 |
| | 0.1 | 5 G-2 | 4.5 | 5 G-1 | 4 |
| | 0.03 | 4 | 3 | 4 | 3 |
| 25 | 0.3 | 5 C-1 | 5 C-1 | 5 G-2 | 5 |
| | 0.1 | 5 | 4.5 G-1 | 5 G-1 | 4.5 G-2 |
| | 0.03 | 4 | 4 | 4 | 3 |
| 28 | 0.3 | 5 | 5 C-1 | 5 G-2 | 5 |
| | 0.1 | 5 G-2 | 5 | 5 | 4.5 |
| | 0.03 | 4 | 4 | 4 | 3 |
| 30 | 0.3 | 5 B-1 | 5 | 5 B-1 | 5 |
| | 0.1 | 4.5 | 4.5 | 5 G-2 | 4.5 |
| | 0.03 | 4 | 4 | 3.5 | 3 |
| 35 | 0.3 | 5 | 4.5 | 5 | 4 |
| | 0.1 | 4.5 | 4 | 4.5 | 3 |
| | 0.03 | 3 | 3 | 3 | 2 |
| 40 (Comparative) | 0.3 | 5 | 4.5 G-1 | 5 | 4 B-1 |
| | 0.1 | 4.5 | 4 | 4 | 2 |
| | 0.03 | 3 | 1 | 2 | 1 |

TEST EXAMPLE 6

Sucker control test on tobacco

Tobacco (*Nicotiana tabacum*) (Yellow) planted in May was pinched after flowering, and the axillary buds were piched by hand. Then, 10 ml of a solution of a predetermined concentration of each compound was sprayed to the top of the stems of the plants. The number of axillary buds per plant, the dry weight of axillary buds per plant and the sucker control ratio were examined two weeks and four weeks after the spraying, and the phytotoxicity was evaluated four weeks after the spraying. The results are shown in Table 7.

The sucker control (%) was computed in accordance with the following equation. The phytotoxicity was evaluated by the same standards as in Test Example 5. Each treated plot contained five plants, and the test results are shown by the mean values.

$$\text{Sucker control ratio (\%)} = \left(1 - \frac{\text{Dry weight of axillary buds per plant in treated plot}}{\text{Dry weight of axillary buds per plant in non-treated plot}}\right) \times 100$$

TABLE 7

Results of Sucker control test on tobacco

| Compound No. | Concentration of active ingredient (%) | Two weeks later from the spraying | | | Four weeks later from the spraying | | | Phytotoxicity |
|---|---|---|---|---|---|---|---|---|
| | | Number of axillary buds per plant | Dry weight of axillary buds per plant (g) | Sucker control ratio (%) | Number of axillary buds per plant | Dry weight of axillary buds per plant (g) | Sucker control ratio (%) | |
| 1 | 0.3 | 2.3 | 0.2 | 95.5 | 2.6 | 0.3 | 98.7 | |
| | 0.1 | 3.0 | 0.3 | 93.2 | 3.3 | 0.4 | 98.3 | |
| | 0.03 | 3.2 | 0.3 | 93.2 | 3.7 | 0.5 | 97.9 | |
| 4 | 0.3 | 1.4 | 0.1 | 97.7 | 2.2 | 0.3 | 98.7 | |

TABLE 7-continued

Results of Sucker control test on tobacco

| Compound No. | Concentration of active ingredient (%) | Two weeks later from the spraying | | | Four weeks later from the spraying | | | Phytotoxicity |
|---|---|---|---|---|---|---|---|---|
| | | Number of axillary buds per plant | Dry weight of axillary buds per plant (g) | Sucker control ratio (%) | Number of axillary buds per plant | Dry weight of axillary buds per plant (g) | Sucker control ratio (%) | |
| | 0.1 | 2.4 | 0.2 | 95.5 | 2.7 | 0.3 | 98.7 | |
| | 0.03 | 3.1 | 0.3 | 93.2 | 3.5 | 0.4 | 98.3 | |
| 8 | 0.3 | 1.7 | 0.1 | 97.7 | 2.0 | 0.2 | 99.2 | C-1 |
| | 0.1 | 2.5 | 0.2 | 95.5 | 2.6 | 0.3 | 98.7 | |
| | 0.03 | 2.8 | 0.2 | 95.5 | 2.8 | 0.3 | 98.7 | |
| 22 | 0.3 | 1.5 | 0.1 | 97.7 | 1.7 | 0.2 | 99.2 | C-1 |
| | 0.1 | 2.3 | 0.2 | 95.5 | 2.8 | 0.3 | 98.7 | |
| | 0.03 | 2.9 | 0.2 | 95.5 | 3.6 | 0.3 | 98.7 | |
| 28 | 0.3 | 2.2 | 0.2 | 95.5 | 2.5 | 0.3 | 98.7 | |
| | 0.1 | 2.8 | 0.3 | 93.2 | 3.1 | 0.4 | 98.3 | |
| | 0.03 | 3.5 | 0.3 | 93.2 | 3.8 | 0.5 | 97.9 | |
| 34 | 0.3 | 1.8 | 0.1 | 97.7 | 2.1 | 0.3 | 98.7 | C-1 |
| | 0.1 | 2.2 | 0.2 | 95.5 | 2.8 | 0.3 | 98.7 | |
| | 0.03 | 3.0 | 0.3 | 93.2 | 3.2 | 0.4 | 98.3 | |
| 40 | 0.3 | 2.7 | 0.3 | 93.2 | 3.2 | 0.5 | 97.9 | |
| Comparative | 0.1 | 3.1 | 0.3 | 93.2 | 3.4 | 2.3 | 90.3 | |
| | 0.03 | 3.7 | 0.5 | 88.6 | 3.8 | 5.1 | 78.3 | |
| No treatment | — | 9.3 | 4.4 | — | 10.2 | 23.2 | — | |

TEST EXAMPLE 7

Thinning test on apples

A few branchs of an apple tree (Fuji) of 12 years old per plot were selected. A solution of each compound having a predetermined concentration was sprayed to the entire branches in an amount sufficient to wet the entire branches, which corresponds to 20 l/a, by a sprayer. Two months later, mean values of the fructification ratios of fruits in central to fruits in lateral, and the transversal diameters of the tested fruits, were computed and the ratios relative to a non-treated portion were determined. The results are shown in Table 8. The numerical values are indicated by rounding off to decimal place. The value in the brackets ( ) in Table 8 are the actually measured values.

TABLE 8

Results of thinning test on apples

| Compound No. | Concentration of active ingredient (ppm) | Number of tested fruits | | Fructification ratio of tested fruits (%) | | Transversal diameter of fruits |
|---|---|---|---|---|---|---|
| | | Fruits in central | Fruits in lateral | Fruits in central | Fruits in lateral | |
| 1 | 100 | 37 | 91 | 83 | 12 | 111 |
| | 30 | 29 | 120 | 85 | 14 | 109 |
| | 10 | 34 | 95 | 86 | 17 | 108 |
| 6 | 100 | 41 | 118 | 83 | 8 | 109 |
| | 30 | 29 | 103 | 90 | 11 | 114 |
| | 10 | 35 | 92 | 88 | 15 | 107 |
| 8 | 100 | 33 | 89 | 82 | 7 | 113 |
| | 30 | 37 | 95 | 87 | 10 | 108 |
| | 10 | 30 | 103 | 85 | 13 | 109 |
| 22 | 100 | 35 | 88 | 87 | 8 | 110 |
| | 30 | 28 | 115 | 88 | 7 | 115 |
| | 10 | 33 | 94 | 85 | 10 | 108 |
| 24 | 100 | 38 | 120 | 81 | 9 | 112 |
| | 30 | 32 | 81 | 84 | 15 | 109 |
| | 10 | 27 | 108 | 91 | 18 | 109 |
| 31 | 100 | 40 | 76 | 88 | 11 | 111 |
| | 30 | 27 | 89 | 87 | 13 | 109 |
| | 10 | 35 | 117 | 85 | 17 | 108 |
| 40 (Comparative) | 100 | 38 | 81 | 72 | 5 | 107 |
| | 30 | 23 | 130 | 85 | 12 | 106 |
| | 10 | 26 | 79 | 92 | 25 | 104 |
| No treatment | — | 36 | 84 | 91 | 32 | 100 (36.8 mm) |

TEST EXAMPLE 8

Elongation control test on new branches of grape

A field of young trees of grape (Delaware) was divided into plots so that each plot contained three plants. At the second elongation period i.e. middle of August, a diluted solution of each compound was sprayed to the entire young tree in an amount corresponding to 10 l/a. One month after the spraying, the evaluation was conducted by the same standards as in Test Example 5. The results are shown in Table 9.

TABLE 9

Results of elongation control test on new buds of grape

| Compound No. | Concentration of active ingredient (%) | Elongation control degree on new buds | Other responses |
|---|---|---|---|
| 1 | 0.3 | 5 | C-1 |
|   | 0.1 | 4 |   |
|   | 0.03 | 3 |   |
| 2 | 0.3 | 5 |   |
|   | 0.1 | 4 |   |
|   | 0.03 | 2 |   |
| 5 | 0.3 | 5 | C-1 |
|   | 0.1 | 4 |   |
|   | 0.03 | 3 |   |
| 8 | 0.3 | 5 |   |
|   | 0.1 | 4 |   |
|   | 0.03 | 3 |   |
| 12 | 0.3 | 5 |   |
|   | 0.1 | 4 |   |
|   | 0.03 | 3 |   |
| 21 | 0.3 | 5 |   |
|   | 0.1 | 3.5 |   |
|   | 0.03 | 2 |   |
| 22 | 0.3 | 5 | C-1 |
|   | 0.1 | 4 |   |
|   | 0.03 | 3 |   |
| 23 | 0.3 | 5 |   |
|   | 0.1 | 4 |   |
|   | 0.03 | 2 |   |
| 29 | 0.3 | 5 |   |
|   | 0.1 | 4 |   |
|   | 0.03 | 3 |   |
| 33 | 0.3 | 5 |   |
|   | 0.1 | 3.5 |   |
|   | 0.03 | 2 |   |
| 40 (Comparative) | 0.3 | 5 | B-1 |
|   | 0.1 | 3 |   |
|   | 0.03 | 1 |   |

TEST EXAMPLE 9

Sprouting control test on onion

A field of onion (Shonan Gokuwase) transplanted in autumn was divided into plots of 5 m², and at 10 days prior to harvest, a diluted solution of each compound having a predetermined concentration was uniformly sprayed to the plot in an amount corresponding to 5 l/a by a hand sprayer. After harvesting, onions were dried in the sun in a green house without cutting off their leaves for one week and then, stored in a well ventilated storage with a slate roof until autumn. Every one month, the rottening rate and the sprouting rate were computed. 50 onions were stored per plot. The results are shown in Table 10.

TABLE 10

Results of sprouting control test on onion

| Compound No. | Dose of active ingredient (g/a) | One month later Rottening rate (%) | One month later Sprouting rate (%) | Two months later Rottening rate (%) | Two months later Sprouting rate (%) | Three months later Rottening rate (%) | Three months later Sprouting rate (%) | Four months later Rottening rate (%) | Four months later Sprouting rate (%) |
|---|---|---|---|---|---|---|---|---|---|
| 1 | 20 | 5 | 0 | 7 | 0 | 10 | 0 | 14 | 0 |
|   | 10 | 4 | 0 | 8 | 0 | 12 | 0 | 16 | 2 |
|   | 5 | 8 | 1 | 9 | 2 | 14 | 4 | 16 | 8 |
| 3 | 20 | 7 | 0 | 9 | 0 | 12 | 0 | 16 | 0 |
|   | 10 | 4 | 0 | 9 | 0 | 14 | 1 | 13 | 3 |
|   | 5 | 5 | 0 | 8 | 1 | 14 | 2 | 16 | 8 |
| 6 | 20 | 3 | 0 | 8 | 0 | 10 | 0 | 12 | 0 |
|   | 10 | 5 | 0 | 9 | 0 | 13 | 1 | 15 | 2 |
|   | 5 | 5 | 0 | 9 | 1 | 15 | 2 | 18 | 6 |
| 7 | 20 | 5 | 0 | 7 | 0 | 10 | 0 | 12 | 0 |
|   | 10 | 5 | 0 | 8 | 0 | 12 | 0 | 14 | 1 |
|   | 5 | 7 | 0 | 9 | 1 | 14 | 2 | 16 | 4 |
| 9 | 20 | 5 | 0 | 7 | 0 | 12 | 0 | 14 | 0 |
|   | 10 | 8 | 0 | 10 | 1 | 14 | 4 | 18 | 8 |
|   | 5 | 9 | 1 | 12 | 2 | 16 | 6 | 18 | 14 |
| 14 | 20 | 4 | 0 | 6 | 0 | 10 | 0 | 12 | 0 |
|   | 10 | 5 | 0 | 8 | 0 | 10 | 0 | 14 | 1 |
|   | 5 | 8 | 0 | 10 | 1 | 12 | 2 | 14 | 4 |
| 20 | 20 | 5 | 0 | 7 | 0 | 10 | 0 | 12 | 0 |
|   | 10 | 7 | 0 | 10 | 1 | 14 | 2 | 16 | 2 |
|   | 5 | 8 | 1 | 12 | 2 | 14 | 4 | 18 | 8 |
| 22 | 20 | 5 | 0 | 7 | 0 | 10 | 0 | 14 | 0 |
|   | 10 | 4 | 0 | 8 | 0 | 12 | 0 | 16 | 2 |
|   | 5 | 8 | 1 | 9 | 2 | 14 | 4 | 16 | 8 |
| 24 | 20 | 7 | 0 | 9 | 0 | 12 | 0 | 16 | 0 |
|   | 10 | 4 | 0 | 9 | 0 | 14 | 1 | 13 | 3 |
|   | 5 | 5 | 0 | 8 | 1 | 14 | 2 | 16 | 8 |
| 27 | 20 | 3 | 0 | 8 | 0 | 10 | 0 | 12 | 0 |
|   | 10 | 5 | 0 | 9 | 0 | 13 | 1 | 15 | 2 |
|   | 5 | 5 | 0 | 9 | 1 | 15 | 2 | 18 | 6 |
| 40 (Comparative) | 20 | 5 | 0 | 10 | 0 | 14 | 1 | 16 | 8 |
|   | 10 | 7 | 1 | 10 | 2 | 14 | 10 | 14 | 20 |
|   | 5 | 5 | 2 | 12 | 6 | 16 | 15 | 18 | 25 |
| No | — | 7 | 4 | 10 | 18 | 22 | 40 | 28 | 62 |

TABLE 10-continued

| | | Results of sprouting control test on onion | | | | | | | |
|---|---|---|---|---|---|---|---|---|---|
| | Dose of active ingredient (g/a) | One month later | | Two months later | | Three months later | | Four months later | |
| Compound No. | | Rotten-ing rate (%) | Sprout-ing rate (%) | Rotten-ing rate (%) | Sprout-ing rate (%) | Rotten-ing rate (%) | Sprout-ing rate (%) | Rotten-ing rate (%) | Sprout-ing rate (%) |
| treatment | | | | | | | | | |

TEST EXAMPLE 10

Inhibition of flower stem development of radish

A field of open-field early-sowing radish (*Raphanus sativus*) (disease resistant and entirely thick) sown in early April, was divided into plots of 5 m². Immediately before flower stem development, a diluted solution of each compound was sprayed to the entire terrestrial foliage in an amount corresponding to 5 l/a. Two weeks later, the flower stem developing rate and flower stem length were evaluated, and one month later, the root weight was evaluated. The evaluations were conducted with respect to 20 plants per plot, and mean values of the flower stem lengths and the root weights were computed. The results are shown in Table 11. The numerical numbers are indicated by rounding off to desimal place, and the values in the brackets ( ) are the actually measured values.

TABLE 11

| | Results of inhibition of flower stem development on radish | | | |
|---|---|---|---|---|
| Compound No. | Dose of active ingredient (g/a) | Flower stem developing rate (%) | Flow stem length (cm) | Root weight (g) |
| 1 | 10 | 15 | 5.5 | 285 |
| | 5 | 30 | 7.2 | 323 |
| 8 | 10 | 10 | 4.5 | 331 |
| | 5 | 30 | 8.0 | 290 |
| 19 | 10 | 20 | 7.3 | 282 |
| | 5 | 40 | 13.5 | 305 |
| 22 | 10 | 15 | 5.3 | 315 |
| | 5 | 30 | 8.5 | 297 |

TABLE 11-continued

| | Results of inhibition of flower stem development on radish | | | |
|---|---|---|---|---|
| Compound No. | Dose of active ingredient (g/a) | Flower stem developing rate (%) | Flow stem length (cm) | Root weight (g) |
| 28 | 10 | 20 | 5.8 | 308 |
| | 5 | 35 | 9.8 | 275 |
| 31 | 10 | 20 | 6.6 | 295 |
| | 5 | 40 | 11.5 | 330 |
| 40 (Comparative) | 10 | 20 | 7.0 | 278 |
| | 5 | 75 | 31.6 | 340 |
| No treatment | — | 90 | 35.6 | 290 |

TEST EXAMPLE 11

Dwarfing test on chrysanthemum

Chrysanthemum (yellow paragon) shoot transplanted in early August was picked two weeks after the transplanting, and then, grown by night lighting. A unit plot consisted of five pots each having a surface area of 200 cm². 5 ml of a solution of each compound having a predetermined concentrations was applied to each pot. The evaluations were conducted one month and two months (flowering period) after the treatment. The results are shown in Table 12. The numerical value represents a ratio of the mean value of five plants relative to the non-treated plot, which is indicated by rounding off to decimal place. The values in the brackets ( ) are the actually measured values.

TABLE 12

| | | Results of dwarfing test on chrysanthemum | | | | | |
|---|---|---|---|---|---|---|---|
| | | One month later | Two months later (flowering period) | | | | |
| Compound No. | Concentration of active ingredient (ppm) | Height of plant (%) | Height of plant (%) | Length of scape (%) | Number of leaves (%) | Effective number of flowers (%) | Time lag of flowering |
| 4 | 600 | 60 | 64 | 61 | 101 | 99 | 2 |
| | 200 | 63 | 70 | 72 | 112 | 105 | 0 |
| 8 | 600 | 53 | 56 | 54 | 108 | 102 | 2 |
| | 200 | 62 | 67 | 63 | 92 | 106 | 0 |
| 11 | 600 | 60 | 65 | 68 | 118 | 110 | 1 |
| | 200 | 68 | 72 | 70 | 105 | 108 | 0 |
| 23 | 600 | 60 | 66 | 52 | 97 | 100 | 2 |
| | 200 | 63 | 71 | 64 | 108 | 101 | 0 |
| 29 | 600 | 55 | 52 | 45 | 110 | 114 | 2 |
| | 200 | 65 | 68 | 60 | 92 | 107 | 0 |
| 34 | 600 | 65 | 70 | 61 | 115 | 105 | 1 |
| | 200 | 78 | 84 | 75 | 102 | 111 | 0 |
| 40 (Comparative) | 600 | 60 | 74 | 70 | 108 | 100 | 1 |
| | 200 | 82 | 90 | 84 | 96 | 103 | 0 |
| No treatment | — | 100 (34.8 cm) | 100 (44.5 cm) | 100 (3.3 cm) | 100 (21.5) | 100 (13.5) | (0) |

TABLE 12-continued

| | | Results of dwarfing test on chrysanthemum | | | | | |
|---|---|---|---|---|---|---|---|
| | Concentration of | One month later | Two months later (flowering period) | | | | |
| Compound No. | active ingredient (ppm) | Height of plant (%) | Height of plant (%) | Length of scape (%) | Number of leaves (%) | Effective number of flowers (%) | Time lag of flowering |
| ment | | | | | | | |

TEST EXAMPLE 12

Foliar treatment test on sugar cane

A field of sugar cane grown to the initial stage of ripening, was divided into unit plots so that each plot contained 6 plants, and a solution having a predetermined concentration was sprayed to the foliage in an amount corresponding to 20 l/a by a small sprayer. Two months later, the heading state was evaluated by the same standards as in Test Example 1, and the sugar content of the pressed juice was measured by means of a polarimetric sugar content meter. The results are shown in Table 13.

TABLE 13

| | Results of foliar treatment test on sugar cane | | |
|---|---|---|---|
| | Concentration of | Results of tests | |
| Compound No. | active ingredient (g/a) | Sugar content (%) | Heading control |
| 1 | 400 | 14.21 | 5 |
| | 200 | 13.88 | 5 |
| | 100 | 13.85 | 4.5 |
| 8 | 400 | 13.98 | 5 |
| | 200 | 13.76 | 5 |
| | 100 | 13.73 | 5 |
| 20 | 400 | 14.02 | 5 |
| | 200 | 13.78 | 5 |
| | 100 | 13.65 | 4.5 |
| 22 | 400 | 14.01 | 5 |
| | 200 | 13.77 | 5 |
| | 100 | 13.65 | 5 |

TABLE 13-continued

| | Results of foliar treatment test on sugar cane | | |
|---|---|---|---|
| | Concentration of | Results of tests | |
| Compound No. | active ingredient (g/a) | Sugar content (%) | Heading control |
| 29 | 400 | 14.13 | 5 |
| | 200 | 13.82 | 5 |
| | 100 | 13.89 | 4.5 |
| 40 (Comparative) | 400 | 13.60 | 5 |
| | 200 | 13.41 | 4.5 |
| | 100 | 13.21 | 4 |
| No treatment | — | 10.41 | 0 |

TEST EXAMPLE 13

Growth control test on weeds in a non-agricultural field

To examine the growth inhibition of large weeds, respective dominant fields of miscanthus (*Miscanthus sinensis*) (Mi) and goldenlod (*Solidago altissima*) (So) were divided into unit plots of 10 m². A diluted solution of each compound was uniformly applied to the entire surface of each plot in an amount corresponding to 100 l/10 ares by a hand sprayer. A micro-granule formulation was applied manually. One month after the application, the growth control was evaluated by the same standards as in Test Example 1. Three months after the application, the heights of the weeds were measured. The results are shown in Table 14.

TABLE 14

| | | Results of growth control test on weeds in a non-agricultural field | | | | | |
|---|---|---|---|---|---|---|---|
| | | | | Height of weeds (cm) | | | |
| | | | | Mi | | So | |
| Compound No. Formulation | Dose of active ingredient (g/a) | Growth control after one month | | At the treatment | Three months later | At the treatment | Three months later |
| | | Mi | So | | | | |
| 1 | 50 | 5 | 5 | 70-100 | 70-100 | 60-70 | 60-80 |
| 50% | 25 | 4.5 | 4 | 70-110 | 80-110 | 70-90 | 80-110 |
| Wettable powder | 12.5 | 4 | 3 | 80-100 | 90-120 | 70-80 | 100-120 |
| 8 | 50 | 5 | 5 | 80-110 | 80-110 | 70-90 | 70-90 |
| 25% | 25 | 5 | 5 | 70-110 | 80-110 | 70-100 | 80-100 |
| Flowable | 12.5 | 4 | 4 | 70-90 | 80-110 | 60-80 | 70-90 |
| 14 | 100 | 5 | 5 | 80-110 | 80-110 | 60-90 | 60-90 |
| 4% Micro-granule formulation F | 50 | 5 | 5 | 70-90 | 70-90 | 60-80 | 70-90 |
| | 25 | 4 | 4 | 80-100 | 90-110 | 70-90 | 80-110 |
| 22 | 100 | 5 | 5 | 70-100 | 70-100 | 70-80 | 70-80 |
| 4% Micro-granule formulation | 50 | 5 | 5 | 80-100 | 90-100 | 70-90 | 80-100 |
| | 25 | 4 | 4 | 70-110 | 80-120 | 60-70 | 80-120 |
| 28 | 50 | 5 | 5 | 80-100 | 70-100 | 60-80 | 60-90 |
| 25% | 25 | 5 | 4 | 70-100 | 70-100 | 60-90 | 80-100 |
| Emulsifiable concentrate | 12.5 | 4 | 3 | 70-110 | 80-120 | 70-90 | 100-140 |
| 35 | 50 | 5 | 5 | 80-110 | 90-100 | 60-90 | 70-90 |

TABLE 14-continued

Results of growth control test on weeds in a non-agricultural field

| Compound No. Formulation | Dose of active ingredient (g/a) | Growth control after one month Mi | Growth control after one month So | Height of weeds (cm) Mi At the treatment | Height of weeds (cm) Mi Three months later | Height of weeds (cm) So At the treatment | Height of weeds (cm) So Three months later |
|---|---|---|---|---|---|---|---|
| 50% Wettable powder | 25 | 4.5 | 4 | 70–100 | 90–110 | 70–90 | 90–110 |
| | 12.5 | 4 | 3 | 70–90 | 80–110 | 60–80 | 90–130 |
| 40 50% Wettable powder (Comparative) | 50 | 5 | 5 | 70–110 | 80–110 | 70–90 | 80–100 |
| | 25 | 4 | 3 | 80–110 | 90–120 | 70–100 | 100–150 |
| | 12.5 | 2 | 1 | 70–100 | 130–170 | 70–90 | 150–180 |
| No treatment | — | 0 | 0 | 60–100 | 180–220 | 60–90 | 180–200 |

TEST EXAMPLE 14

Test for effect of prolonging the life of cut flowers

Cut flowers of carnation (*Diauthus caryophllus*) at bud period were divided into unit plots so that each plot contained three cut flowers, and the test was conducted by the following two methods.

(1) A diluted solution of each compound was prepared by an addition of each compound to 200 ml of water in a flower vase so that the diluted solution had a predetermined concentration, and cut flowers were put in the vase.

(2) A bud part of cut flowers was immersed in a solution of each compound having a predetermined concentration for a few seconds, the solution was softly shaken off, and the cut flowers were put in the vase.

During the test period, sterilized water was added to the flower vases.

The effect for prolonging the life of cut flowers was indicated by the number of days from the time when the flowers of a non-treated plot became no longer acceptable for display i.e. 9 days after the beginning of the test. The evaluation of the phytotoxicities such as withering were conducted one week after the beginning of the test in accordance with the following standards.

| Withering of leaves: | Slight | L-1 |
| | Little | L-2 |
| | Substantial | L-3 |
| Withering of petal: | Slight | P-1 |
| | Little | P-2 |
| | Substantial | P-3 |

The results are shown in Table 15.

TABLE 15

Test for effect of prolonging the life of cut flowers

| Compound No. | Concentration of active ingredient (ppm) | (1) Water absorption method Effect of prolonging the life | (1) Water absorption method Phytotoxicity | (2) Immersing method Effect of prolonging the life | (2) Immersing method Phytotoxicity |
|---|---|---|---|---|---|
| 1 | 50 | 8 | L-1 | 10 | |
| | 25 | 8 | | 9 | |
| | 12.5 | 7 | | 8 | |
| 3 | 50 | 8 | | 9 | |
| | 25 | 9 | | 8 | |
| | 12.5 | 8 | | 8 | |
| 14 | 50 | 7 | | 9 | |
| | 25 | 6 | | 7 | |
| | 12.5 | 6 | | 8 | |
| 20 | 50 | 9 | L-1 | 9 | |
| | 25 | 10 | | 9 | |
| | 12.5 | 9 | | 8 | |
| 22 | 50 | 8 | L-1 | 10 | |
| | 25 | 8 | | 9 | |
| | 12.5 | 8 | | 9 | |
| 29 | 50 | 8 | L-1, P-1 | 9 | P-1 |
| | 25 | 8 | | 9 | |
| | 12.5 | 9 | | 8 | |
| 40 (Comparative) | 50 | 6 | L-1 | 7 | |
| | 25 | 6 | | 6 | |
| | 12.5 | 5 | | 5 | |
| No treatment | — | 0 | 0 | — | — |

We claim:

1. A benzamide derivative of the formula:

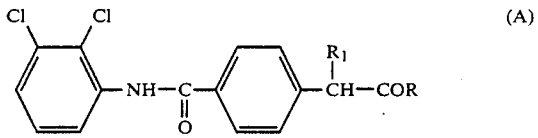

(A)

wherein $R_1$ is hydrogen or methyl, and R is hydroxyl, $C_1$–$C_6$ alkoxy, alkenylalkoxy, alkoxyalkoxy, amino, $C_1$–$C_4$ monoalkylamino, monoalkenylamino, dialkylamino or O-cat wherein cat is a metal, ammonium or an organic cation.

2. A plant growth regulant containing a benzamide derivative of the formula A as defined in claim 1.

3. The benzamide derivative according to claim 1, which is:

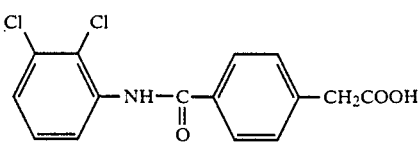

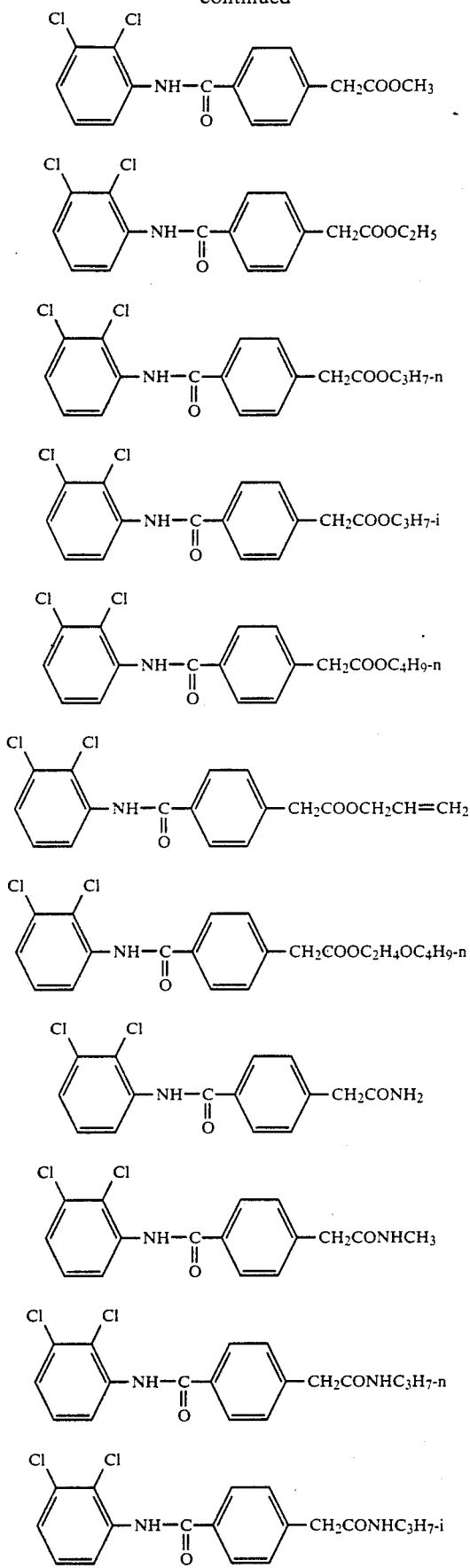
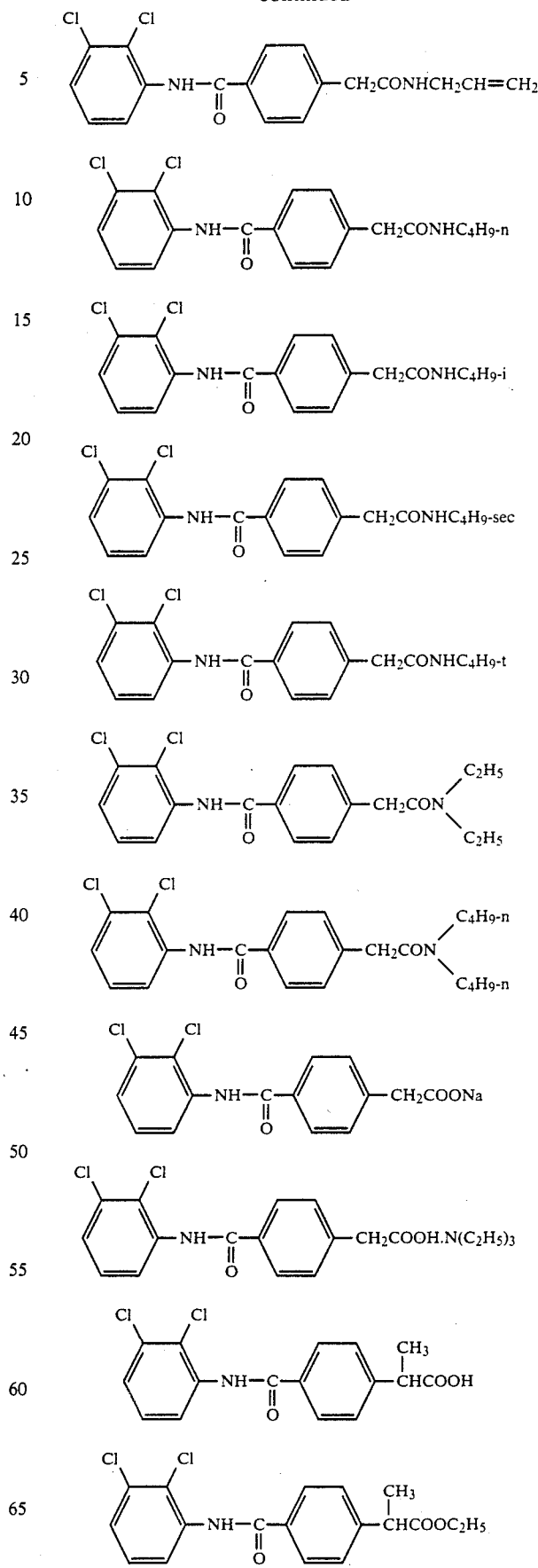

-continued
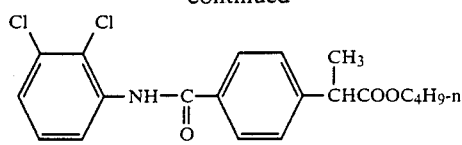
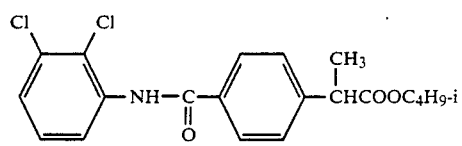
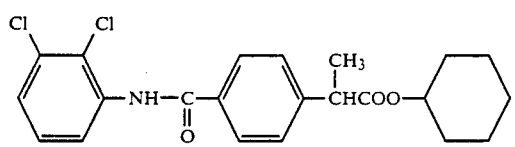
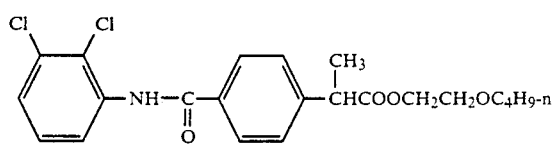
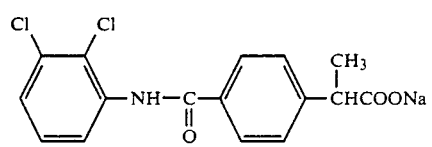
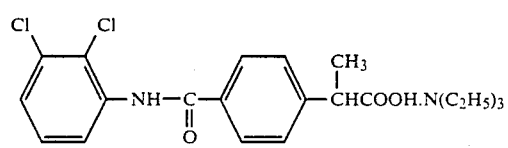
-continued
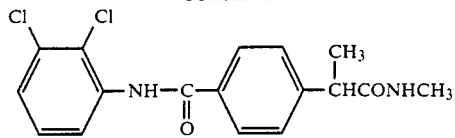
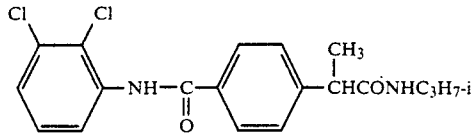
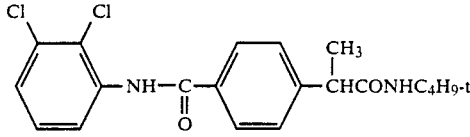
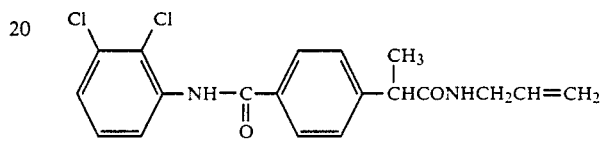
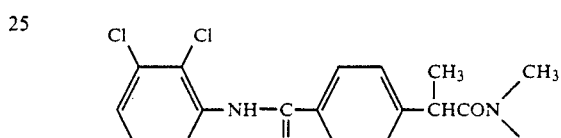
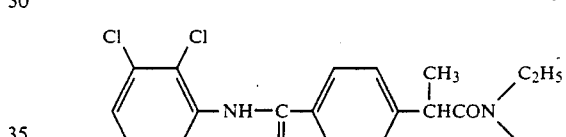
* * * * *